(12) United States Patent
Rector et al.

(10) Patent No.: US 11,202,629 B2
(45) Date of Patent: Dec. 21, 2021

(54) CLAMPING BASED LOCKOUT MECHANISM FOR RIGHT ANGLE SURGICAL STAPLER

(71) Applicant: Ethicon LLC, Guaynabo, PR (US)

(72) Inventors: Jason M. Rector, Maineville, OH (US); Nicholas Fanelli, Morrow, OH (US)

(73) Assignee: Cilag GmbH International, Zug (CH)

( * ) Notice: Subject to any disclaimer, the term of this patent is extended or adjusted under 35 U.S.C. 154(b) by 123 days.

(21) Appl. No.: 16/395,358

(22) Filed: Apr. 26, 2019

(65) Prior Publication Data
US 2020/0337699 A1    Oct. 29, 2020

(51) Int. Cl.
| | |
|---|---|
| *A61B 17/072* | (2006.01) |
| *A61B 17/29* | (2006.01) |
| *A61B 17/10* | (2006.01) |
| *A61B 17/00* | (2006.01) |

(52) U.S. Cl.
CPC ........ *A61B 17/072* (2013.01); *A61B 17/2909* (2013.01); *A61B 17/105* (2013.01); *A61B 2017/0046* (2013.01); *A61B 2017/0725* (2013.01); *A61B 2017/07221* (2013.01); *A61B 2017/07257* (2013.01); *A61B 2017/07271* (2013.01); *A61B 2017/2925* (2013.01)

(58) Field of Classification Search
None
See application file for complete search history.

(56) References Cited

U.S. PATENT DOCUMENTS

| | | | |
|---|---|---|---|
| 4,805,823 | A | 2/1989 | Rothfuss |
| 5,275,323 | A | 1/1994 | Schulze et al. |
| 5,307,976 | A | 5/1994 | Olson et al. |
| 5,415,334 | A | 5/1995 | Williamson, IV et al. |

(Continued)

FOREIGN PATENT DOCUMENTS

| | | |
|---|---|---|
| EP | 0488768 A1 | 6/1992 |
| EP | 1736104 A1 | 12/2006 |
| WO | WO 2012/142872 A1 | 10/2012 |

OTHER PUBLICATIONS

Extended European Search Report dated Jul. 2, 2020 for Application No. 20171333.6, 12 pages.

(Continued)

*Primary Examiner* — Hemant Desai
*Assistant Examiner* — Tanzim Imam
(74) *Attorney, Agent, or Firm* — Frost Brown Todd LLC

(57) ABSTRACT

A surgical stapler includes a body, a shaft assembly, and an end effector at a distal end of the shaft assembly. The end effector is actuatable between an open state for receiving tissue and a closed state for clamping the tissue. A closure system is operable to actuate the end effector from the open state to the closed state. A firing system is operable to actuate the end effector in the closed state to staple the clamped tissue. A firing lockout mechanism is movable between a lockout state that inhibits actuation of the firing system, and a bypass state that permits actuation of the firing system. The firing lockout mechanism is configured to maintain the lockout state until the end effector assumes the closed state, and is further configured to transition from the lockout state to the bypass state in response to the end effector assuming the closed state.

20 Claims, 30 Drawing Sheets

(56) References Cited

U.S. PATENT DOCUMENTS

| | | | |
|---|---|---|---|
| 5,465,895 A | 11/1995 | Knodel et al. | |
| 5,487,500 A | 1/1996 | Knodel et al. | |
| 5,597,107 A | 1/1997 | Knodel et al. | |
| 5,605,272 A | 2/1997 | Witt et al. | |
| 5,632,432 A | 5/1997 | Schulze et al. | |
| 5,653,373 A | 8/1997 | Green et al. | |
| 5,662,258 A | 9/1997 | Knodel et al. | |
| 5,662,667 A | 9/1997 | Knodel | |
| 5,673,840 A | 10/1997 | Schulze et al. | |
| 5,697,543 A | 12/1997 | Burdorff | |
| 5,704,534 A | 1/1998 | Huitema et al. | |
| 5,762,255 A * | 6/1998 | Chrisman | A61B 17/07207 227/175.2 |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 5,878,938 A | 3/1999 | Bittner et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,905,057 B2 | 6/2005 | Swayze et al. | |
| 6,959,852 B2 | 11/2005 | Shelton, IV et al. | |
| 6,978,921 B2 | 12/2005 | Shelton, IV et al. | |
| 6,988,649 B2 | 1/2006 | Shelton, IV et al. | |
| 6,988,650 B2 | 1/2006 | Schwemberger et al. | |
| 7,000,818 B2 | 2/2006 | Shelton, IV et al. | |
| 7,044,352 B2 | 5/2006 | Shelton, IV et al. | |
| 7,083,075 B2 | 8/2006 | Swayze et al. | |
| 7,134,587 B2 | 11/2006 | Schwemberger et al. | |
| 7,143,923 B2 | 12/2006 | Shelton, IV et al. | |
| 7,143,926 B2 | 12/2006 | Shelton, IV et al. | |
| 7,147,139 B2 | 12/2006 | Schwemberger et al. | |
| 7,147,140 B2 | 12/2006 | Wukusick et al. | |
| 7,204,404 B2 | 4/2007 | Nguyen et al. | |
| 7,207,472 B2 | 4/2007 | Wukusick et al. | |
| 7,303,108 B2 | 12/2007 | Shelton, IV et al. | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,419,080 B2 | 9/2008 | Smith et al. | |
| 7,434,715 B2 | 10/2008 | Shelton, IV et al. | |
| 7,455,208 B2 | 11/2008 | Wales et al. | |
| 7,490,749 B2 | 2/2009 | Schall et al. | |
| 7,524,320 B2 | 4/2009 | Tierney et al. | |
| 7,549,564 B2 | 6/2009 | Boudreaux | |
| 7,644,848 B2 | 1/2010 | Swayze et al. | |
| 7,658,311 B2 | 2/2010 | Boudreaux | |
| 7,691,098 B2 | 4/2010 | Wallace et al. | |
| 7,721,930 B2 | 5/2010 | McKenna et al. | |
| 7,753,245 B2 | 7/2010 | Boudreaux et al. | |
| 7,798,386 B2 | 9/2010 | Schall et al. | |
| 7,806,891 B2 | 10/2010 | Nowlin et al. | |
| 7,954,684 B2 | 6/2011 | Boudreaux | |
| 8,210,411 B2 | 7/2012 | Yates et al. | |
| 8,245,898 B2 | 8/2012 | Smith et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,579,176 B2 | 11/2013 | Smith et al. | |
| 8,602,288 B2 | 12/2013 | Shelton, IV et al. | |
| 8,608,046 B2 | 12/2013 | Laurent et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 9,186,142 B2 | 11/2015 | Fanelli et al. | |
| 9,517,065 B2 | 12/2016 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,867,615 B2 | 1/2018 | Fanelli et al. | |
| 10,045,780 B2 | 8/2018 | Adams et al. | |
| 10,092,292 B2 | 10/2018 | Boudreaux et al. | |
| 2005/0023324 A1* | 2/2005 | Doll | A61B 17/07207 227/175.2 |
| 2006/0180634 A1 | 8/2006 | Shelton, IV et al. | |
| 2007/0010838 A1 | 1/2007 | Shelton, IV et al. | |
| 2007/0073341 A1 | 3/2007 | Smith et al. | |
| 2007/0084897 A1 | 4/2007 | Shelton, IV et al. | |
| 2007/0175955 A1 | 8/2007 | Shelton, IV et al. | |
| 2008/0099530 A1 | 5/2008 | Olson et al. | |
| 2010/0193567 A1 | 8/2010 | Scheib et al. | |
| 2011/0084112 A1 | 4/2011 | Kostrzewski | |
| 2011/0155780 A1* | 6/2011 | Boudreaux | A61B 17/07207 227/175.2 |
| 2011/0163147 A1 | 7/2011 | Laurent et al. | |
| 2011/0290853 A1 | 12/2011 | Shelton, IV et al. | |
| 2012/0138660 A1 | 6/2012 | Shelton, IV et al. | |
| 2012/0181322 A1 | 7/2012 | Whitman et al. | |
| 2012/0199630 A1 | 8/2012 | Shelton, IV et al. | |
| 2012/0199632 A1 | 8/2012 | Spivey et al. | |
| 2012/0203247 A1 | 8/2012 | Shelton, IV et al. | |
| 2013/0012957 A1 | 1/2013 | Shelton, IV et al. | |

OTHER PUBLICATIONS

International Search Report and Written Opinion dated Jul. 2, 2020 for International Application No. PCT/IB2020/053513, 20 Pages.

Chinese Office Action, Notification of the First Office Action, dated Feb. 28, 2017 for Application No. 2014800108866, 7 pages.

Extended European Search Report dated May 16, 2014 for Application No. 14157358.

Extended European Search Report and Written Opinion dated Nov. 8, 2016 for Application No. EP 16176672.0, 8 pages.

International Search Report and Written Opinion dated May 27, 2014 for International Application No. PCT/US2014/016202, 6 pages.

International Preliminary Report on Patentability dated Sep. 1, 2015 for International Application No. PCT/US2014/016202, 9 pages.

U.S. Appl. No. 16/234,740, entitled "Surgical Stapler with Sloped Staple Deck for Varying Tissue Compression," filed Dec. 28, 2018.

U.S. Appl. No. 16/395,357, entitled "Tissue Cutting Washer for Right Angle Surgical Stapler," filed Apr. 26, 2019.

U.S. Appl. No. 16/395,359, entitled "Cartridge Based Lockout Mechanism for Right Angle Surgical Stapler," filed Apr. 26, 2019.

U.S. Appl. No. 16/395,364, entitled "Staple Retainer for Surgical Stapler Cartridge," filed Apr. 26, 2019.

U.S. Appl. No. 16/583,690, entitled "Circular Surgical Stapler," filed Sep. 26, 2019.

Design U.S. Appl. No. 29/689,028, entitled "Staple Retainer for Surgical Stapler Cartridge," filed Apr. 26, 2019.

* cited by examiner

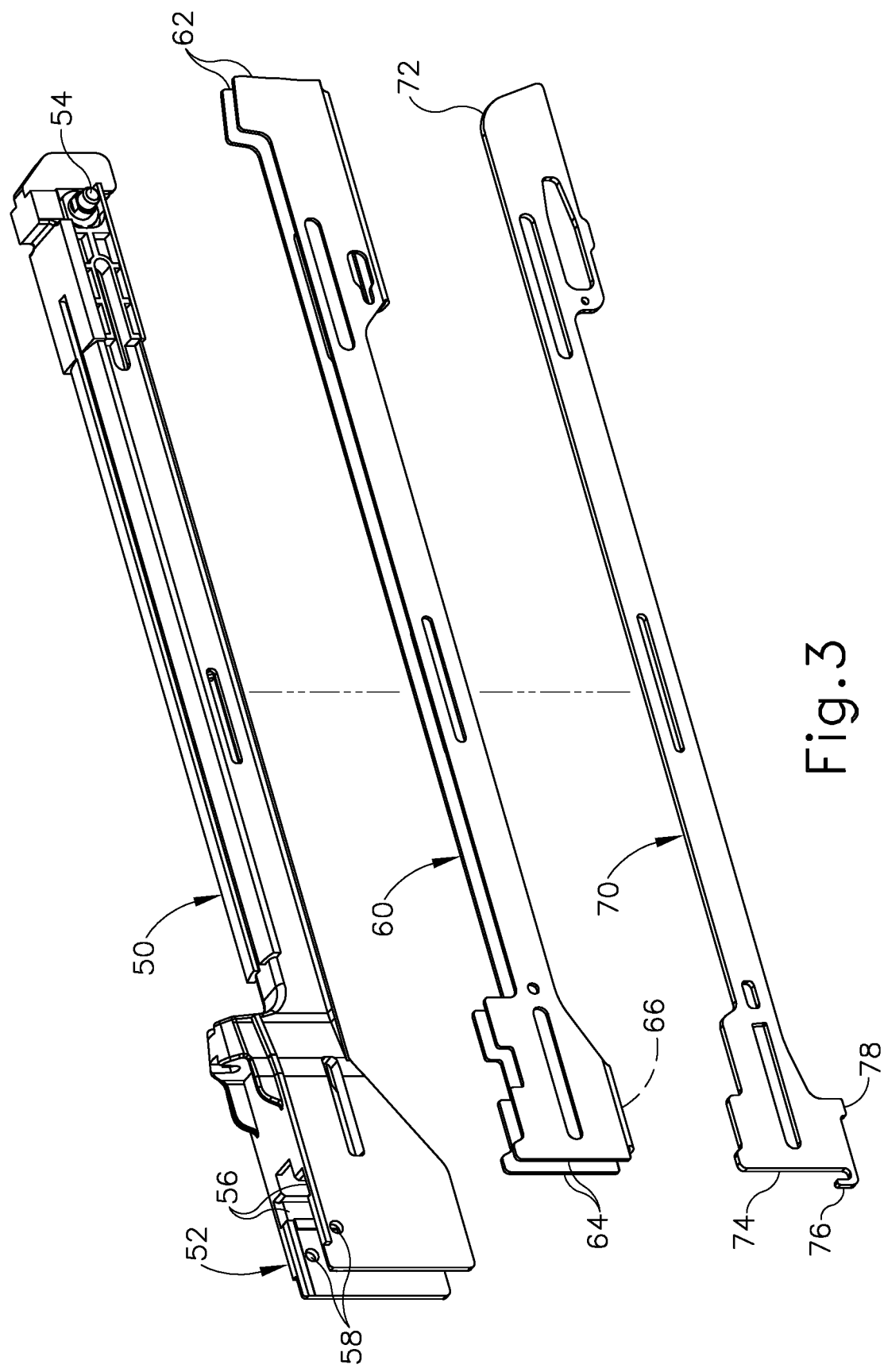

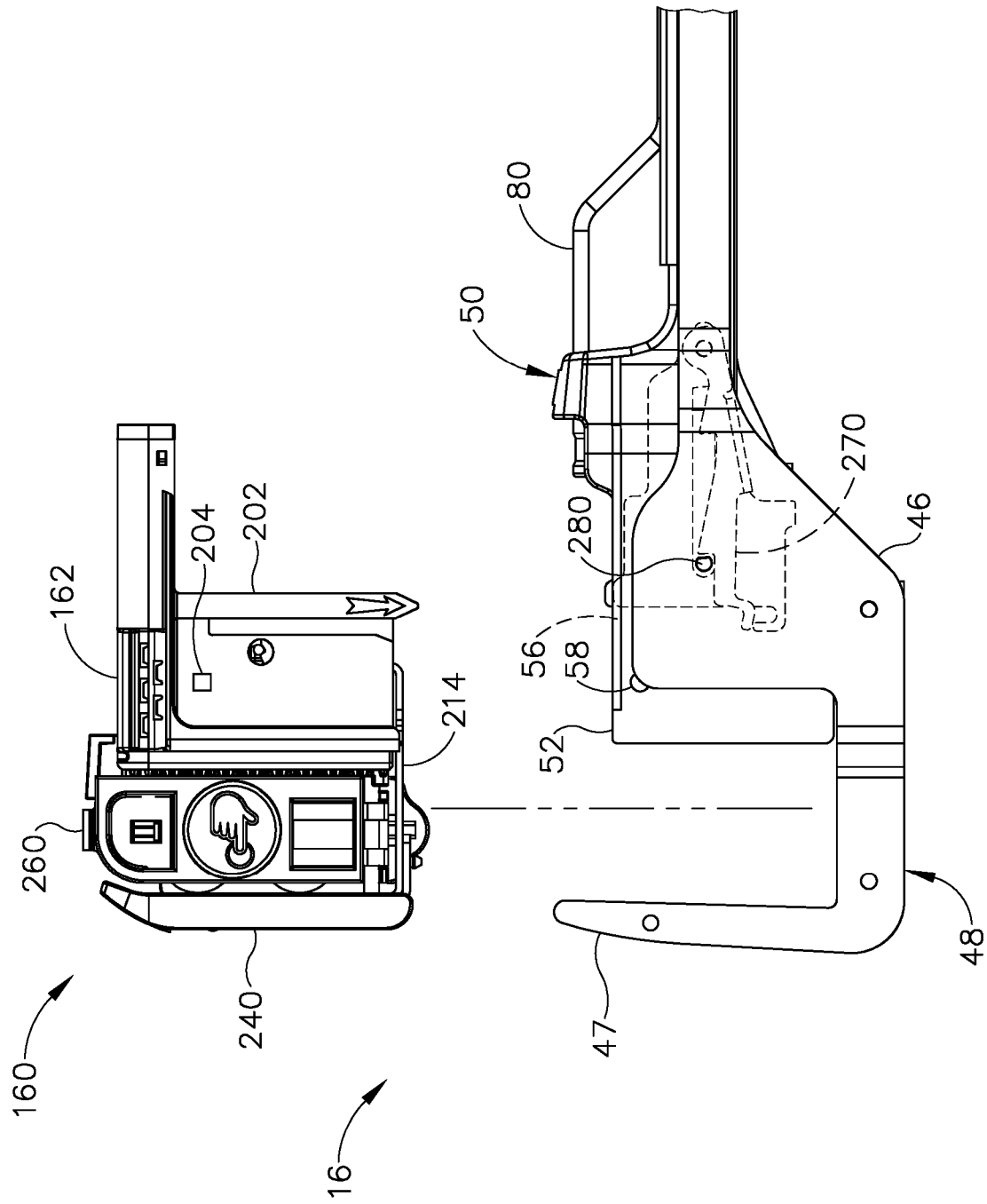

CLAMPING BASED LOCKOUT MECHANISM FOR RIGHT ANGLE SURGICAL STAPLER

BACKGROUND

Some surgical staplers are operable to clamp down on one or more layers of patient tissue, form staples through the layers of tissue to substantially seal the layers of tissue together near the formed staples, and cut through the layers of clamped tissue for forming severed ends of operatively sealed tissue. An exemplary stapling instrument includes a pair of cooperating elongate jaw members, where each jaw member is adapted to be inserted into a patient and positioned relative to tissue that is to be stapled. One of the jaw members supports a staple cartridge having at least two laterally spaced rows of staples contained therein, and the other jaw member supports an anvil having staple-forming pockets configured to align with the rows of staples in the staple cartridge. Generally, the stapling instrument further includes one or more pusher bars that are actuatable relative to the jaw members to drive staples from the staple cartridge, through tissue clamped between the jaw members, and against the anvil for forming, and also to drive a knife member through the clamped tissue and thereby cut the tissue simultaneously with or subsequent to the stapling. In this manner, the stapling instrument is operable to form a plurality of laterally spaced rows of deformed staples in the clamped tissue, where such rows may comprise linear rows and/or arcuate rows. The knife blade may cut the tissue along a linear or arcuate path that extends between adjacent rows of the staples formed in the clamped tissue.

Merely exemplary surgical staplers are disclosed in U.S. Pat. No. 5,605,272, entitled "Trigger Mechanism for Surgical Instruments," issued Feb. 25, 1997; U.S. Pat. No. 5,697,543, entitled "Linear Stapler with Improved Firing Stroke," issued Dec. 16, 1997; U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007; and U.S. Pat. No. 10,045,780, entitled "Method of Applying Staples in Lower Anterior Bowel Resection," issued Aug. 14, 2018. The disclosure of each of the above-cited U.S. patents and U.S. patent publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3 depicts a disassembled perspective view of actuatable components of the shaft assembly of the surgical stapler of FIG. 1A, including a closure bar of the closure system, a staple bar of the firing system, and a knife bar of the firing system;

FIG. 9A depicts a side elevational view of the end effector of the surgical stapler of FIG. 1A, showing a lockout member of the end effector in a lockout position when a staple cartridge unit is absent from the distal support structure;

Figure 1A:
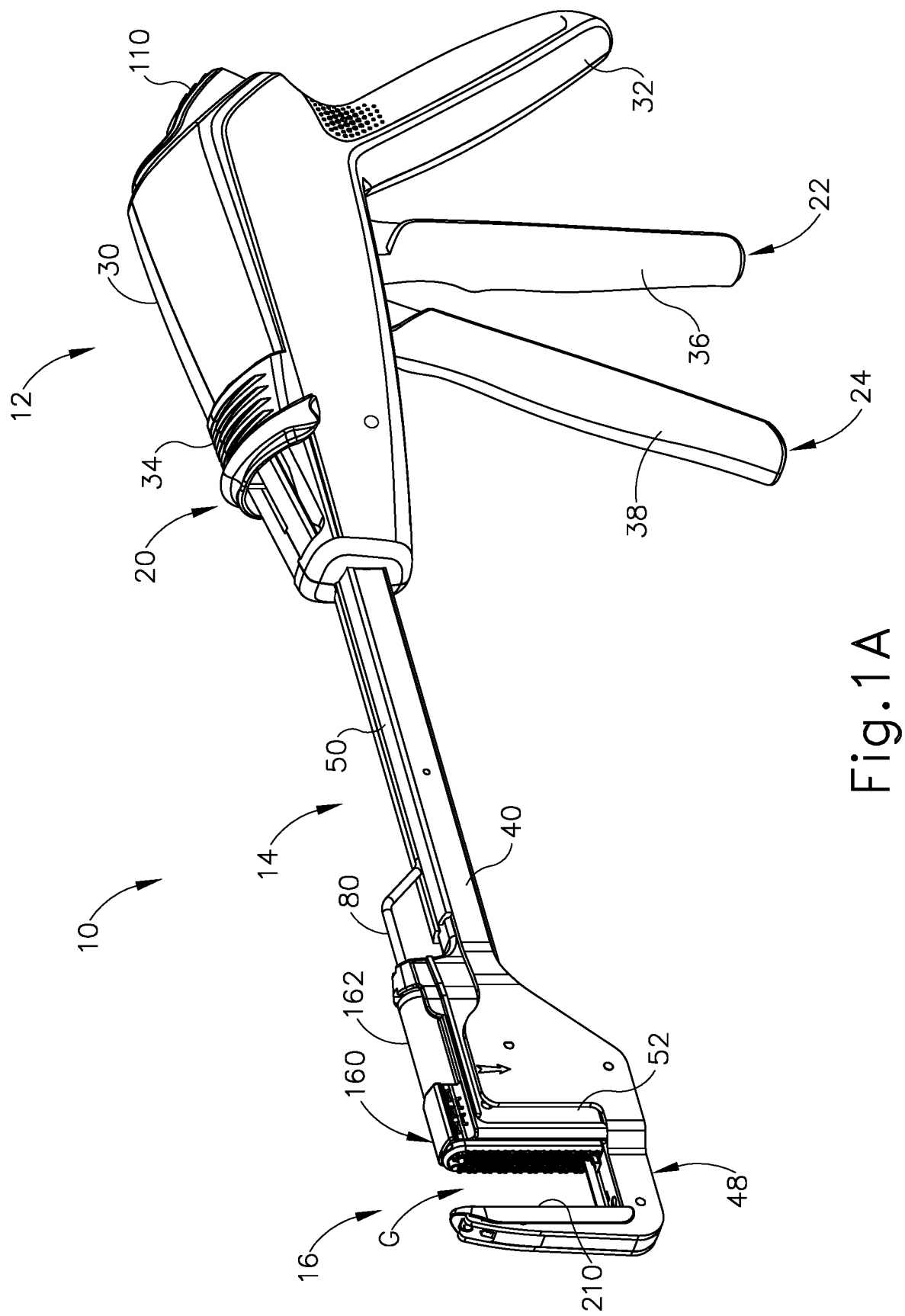
FIG. 1A depicts a perspective view of an exemplary surgical stapler having a handle assembly, a shaft assembly, and an end effector, showing a tissue retaining pin actuation system in a retracted position and the end effector in an open state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," "left," "right" or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about," "approximately," and the like in connection with any numerical values or ranges of values are intended to encompass the exact value(s)

referenced, as well as a suitable dimensional tolerance that enables the referenced feature or combination of features to function for the intended purpose described herein.

I. Overview of Exemplary Right Angle Surgical Stapler

FIG. 1A depicts an exemplary right angle linear surgical stapler (10) that is configured to staple and cut tissue in various non-endoscopic ("open") surgical procedures, including colorectal, thoracic, and bariatric procedures, for example. Right angle linear surgical stapler (10) (also referred to as a "right angle linear cutter") generally includes a handle assembly (12), a shaft assembly (14) extending distally from handle assembly (12), and an end effector (16) at a distal end of shaft assembly (14). As described below, end effector (16) is provided with a "right angle" configuration such that end effector (16) clamps, staples, and cuts tissue in a plane that extends transversely at a right angle to a longitudinal axis defined by shaft assembly (14).

As described in greater detail below, surgical stapler (10) includes several actuation systems for operating end effector (16) via handle assembly (12) during a surgical procedure on a patient. In particular, surgical stapler (10) includes a tissue retaining pin actuation system (20) operable to initially retain tissue within end effector (16); a closure system (22) operable to clamp tissue with end effector (16); and a firing system (24) operable to subsequently staple and cut tissue with end effector (16).

While the teachings herein are shown and described in the context of a "linear" surgical stapler (10) configured to apply linear rows of staples and a linear cut line in tissue, it will be appreciated that any one or more of the teachings herein may be applied to a surgical stapler configured to apply staple rows and a tissue cut line with a non-linear (e.g., curved) configuration, such as a surgical stapler of the type disclosed in any one or more of the references incorporated by reference herein.

A. Handle Assembly and Shaft Assembly of Surgical Stapler

Figure 1B:
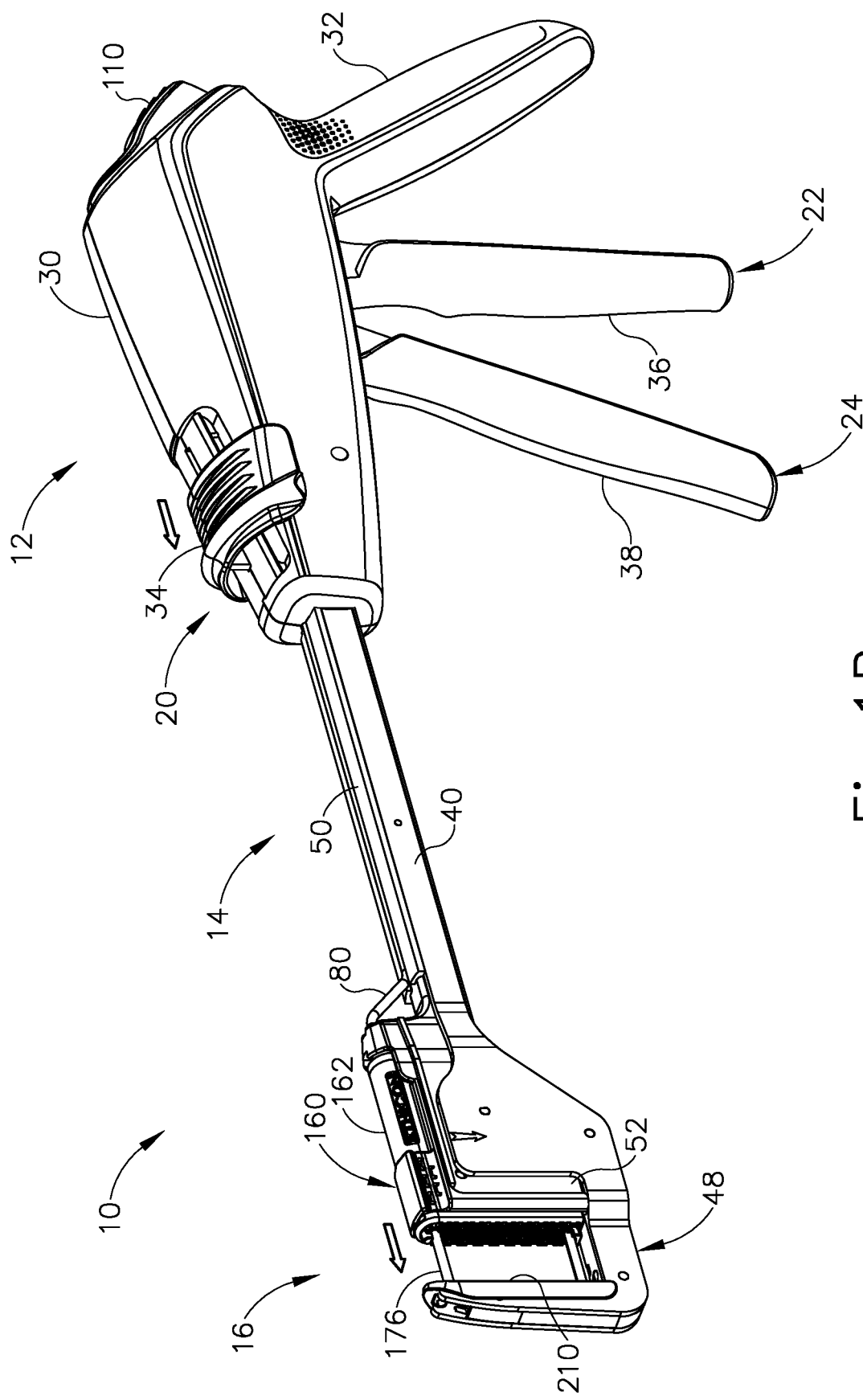
FIG. 1B depicts a perspective view of the surgical stapler of FIG. 1A, showing the tissue retaining pin actuation system in an extended position while the end effector remains in the open state.
Figure 1C:
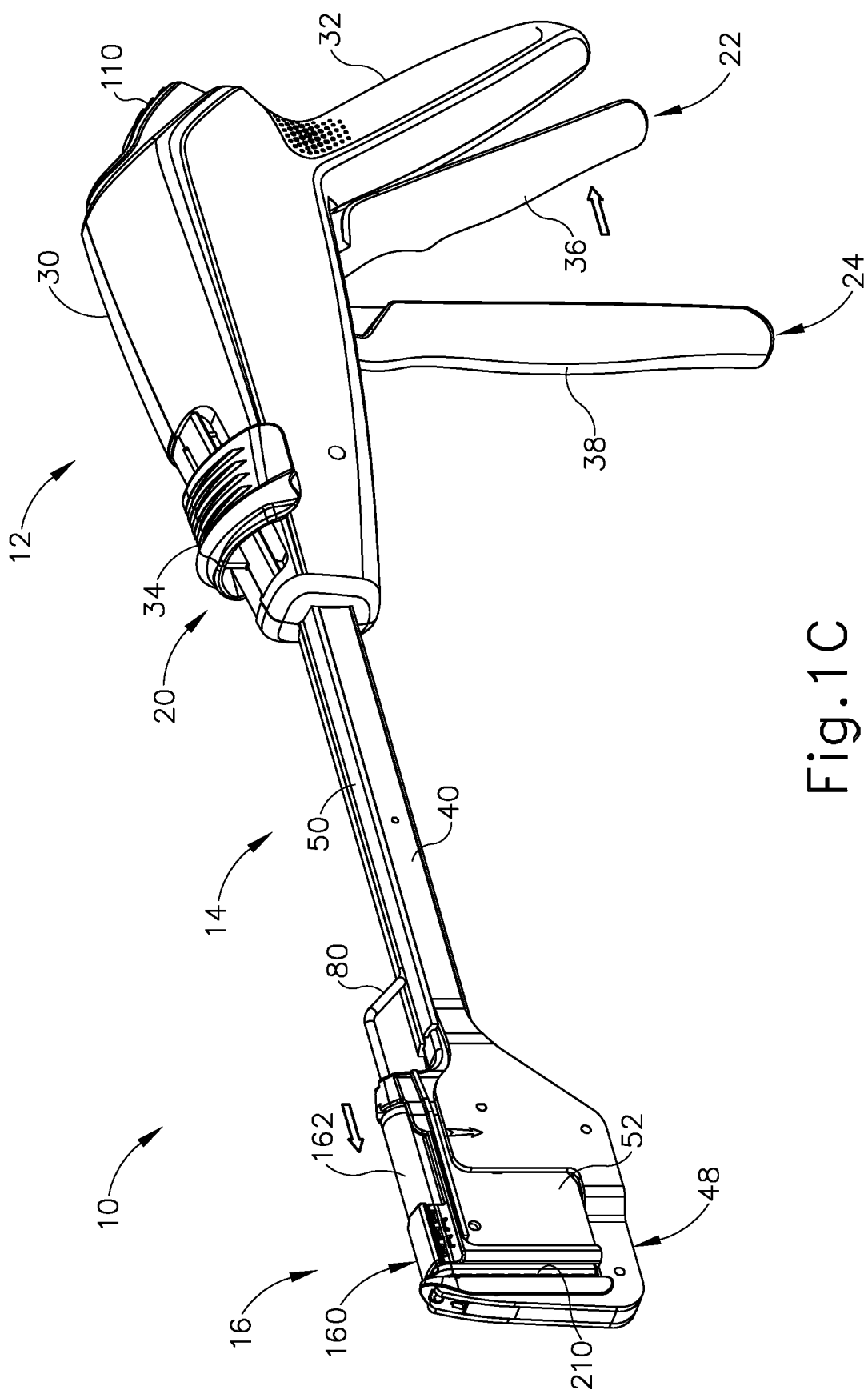
FIG. 1C depicts a perspective view of the surgical stapler of FIG. 1A, showing the end effector in a closed state via actuation of a closure system, while the tissue retaining pin actuation system remains in the extended position.
Figure 1D:
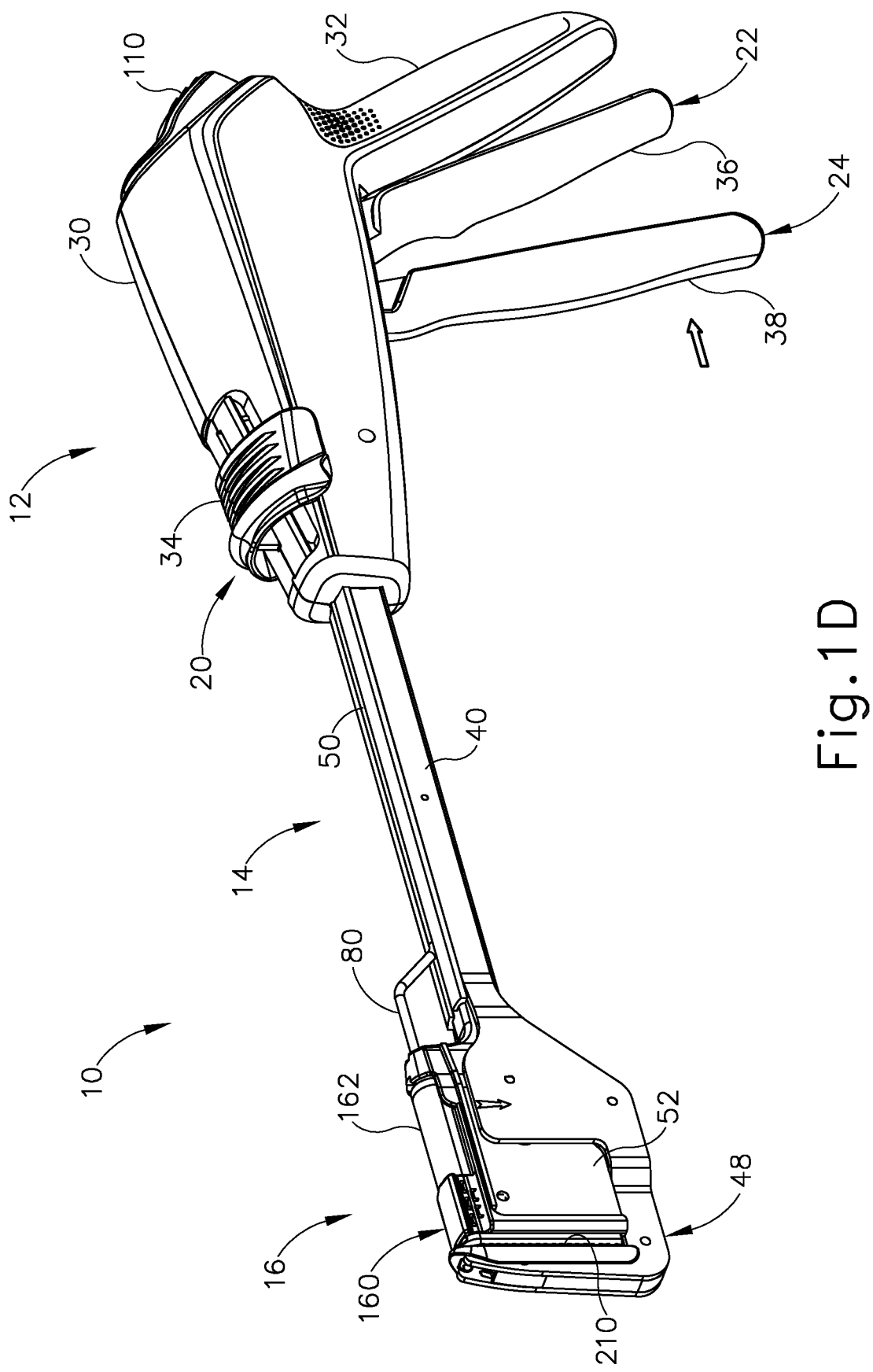
FIG. 1D depicts a perspective view of the surgical stapler of FIG. 1A, showing the end effector in a fired state via actuation of a firing system to effect stapling and cutting of tissue captured by the end effector, while the tissue retaining pin actuation system remains in the extended position.

As shown in FIG. 1A, handle assembly (12) includes a housing (30) that defines a pistol grip (32), a saddle shaped slide (34) slidably disposed on an upper portion of handle housing (30), a pivotable closure trigger (36), and a pivotable firing trigger (38). Closure trigger (36) and firing trigger (38) are operatively coupled with end effector (16) via shaft assembly (14) such that end effector (16) is configured to close and thereby clamp tissue in response to actuation of closure trigger (36), and subsequently staple and cut tissue (i.e., "fire") in response to actuation of firing trigger (38). FIG. 1A shows slide (34) and closure trigger (36) in unactuated configurations such that end effector (16) is configured to receive tissue laterally within a gap (G) (or "aperture") defined between a cartridge housing (162) and an anvil (210) of a replaceable staple cartridge unit (160) (or "reload") mounted within end effector (16). As shown in FIG. 1B, translating slide (34) distally toward end effector (16) extends a tissue retaining pin (176) of staple cartridge unit (160) distally for capturing the tissue between anvil (210) and cartridge housing (162). As shown in FIG. 1C, subsequently actuating closure trigger (36) toward pistol grip (32) drives cartridge housing (162) distally toward anvil (210), thereby clamping tissue therebetween. As shown in FIG. 1D, subsequently actuating firing trigger (38) toward pistol grip (32) drives staples distally into the clamped tissue and also cuts the tissue between formed staple lines with a knife member (194) (see FIG. 8), as described in greater detail below.

Figure 2:
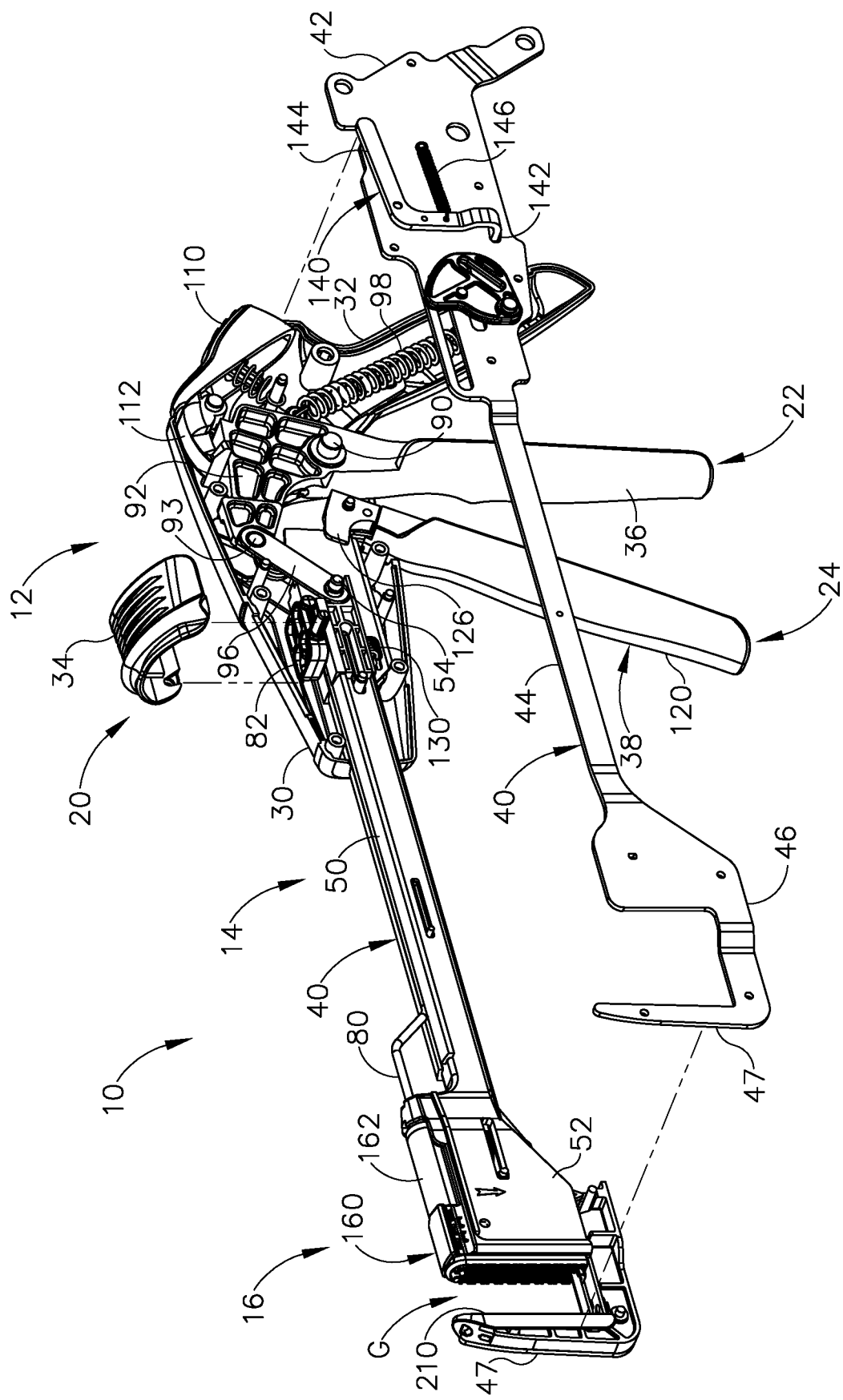
FIG. 2 depicts a partially disassembled perspective view of the surgical stapler of FIG. 1A.

As shown in FIG. 2, surgical stapler (10) includes a pair of longitudinally extending side plates (40) that cooperate to define a frame structure of stapler (10) that supports tissue retaining pin actuation system (20), closure system (22), and firing system (24). Each side plate (40) includes a proximal frame portion (42) housed within handle housing (30); a medial shaft portion (44) that defines a respective outer lateral side of shaft assembly (14); and a distal jaw portion (46) having an upwardly extending distal hook (47). Distal jaw portions (46) cooperate with the distal end of a closure bar (50), described below, to define a U-shaped distal support structure (48) of end effector (16) that removably receives staple cartridge unit (160). As used herein, the term "U-shaped" refers to the shape presented by end effector (16) in any of the side elevational views depicted herein.

As shown in FIG. 3, slidably disposed between and supported by side plates (40) are elongate actuatable components of actuation systems (20, 22, 24), which operatively couple handle assembly (12) with staple cartridge unit (160); including a closure bar (50), a staple bar (60), and a knife bar (70). Closure bar (50) includes a cartridge-receiving distal portion (52) configured to receive and support staple cartridge unit (160). Closure bar (50) and staple bar (60) are each configured as a double-sided structure having first and second lateral sides spaced apart from one another, and an inner channel extending longitudinally therebetween. This configuration enables an arrangement of shaft assembly (14) in which knife bar (70) is nested and slidably disposed within the longitudinal inner channel of staple bar (60), and in which staple bar (60) in turn is nested and slidably disposed within the longitudinal inner channel of closure bar (50). Moreover, staple bar (60) and knife bar (70) are longitudinally translatable independently of closure bar (50) through a range of longitudinal motion that enables independent closure and firing of end effector (16). As described in greater detail below, closure bar (50) is operable to actuate cartridge housing (162) longitudinally relative to anvil (210) for clamping tissue in response to actuation of closure trigger (36). Staple bar (60) is operable to actuate a staple driver member (186) (see FIG. 8) longitudinally relative to cartridge housing (162) for stapling the clamped tissue. Knife bar (70) is operable to actuate knife member (194) (see FIG. 8) longitudinally relative to cartridge housing (162) and staple driver member (186) for cutting the clamped tissue.

Tissue retaining pin actuation system (20) of surgical stapler (10) includes slide (34) of handle assembly (12), tissue retaining pin (176) of staple cartridge unit (160), an elongate pushrod (80) extending longitudinally along an upper side of shaft assembly (14), and a pushrod driver (82) slidably disposed within handle assembly (12). A distal end of pushrod (80) is configured to releasably couple with tissue retaining pin (176) upon insertion of staple cartridge unit (160) into distal support structure (48) of end effector (16). A proximal end of pushrod (80) is coupled with pushrod driver (82), which in turn is coupled with slide (34). Accordingly, longitudinal translation of slide (34) between proximal and distal positions drives longitudinal translation of tissue retaining pin (176) relative to cartridge housing (162) between retracted and extended positions. As shown in FIG. 1A, tissue retaining pin (176) is configured to assume a retracted position in which retaining pin (176) is housed within cartridge housing (162) when slide (34) is in a proximal position. As shown in FIG. 1B, tissue retaining pin (176) is configured to assume an extended position in which a distal end of retaining pin (176) engages anvil (210), thereby retaining tissue positioned within gap (G) of staple cartridge unit (160), when slide (34) is advanced to the distal position.

Closure system (22) of surgical stapler (10) includes closure trigger (36) of handle assembly (12) and closure bar (50). As shown in FIGS. 2 and 4A-4C, closure trigger (36) is pivotably coupled with handle housing (30) about a pair of laterally extending posts (90). An upper arm (92) of closure trigger (36) having a vertically slotted distal portion is operatively coupled with a proximal end of closure bar (50) by a pair of closure links (96). A proximal end of each closure link (96) is pivotably coupled with a laterally extending post (93) of closure trigger upper arm (92). A distal end of each closure link (96) is pivotably coupled with the proximal end of closure bar (50) about a laterally extending post (54) of closure bar (50).

Figure 4A:
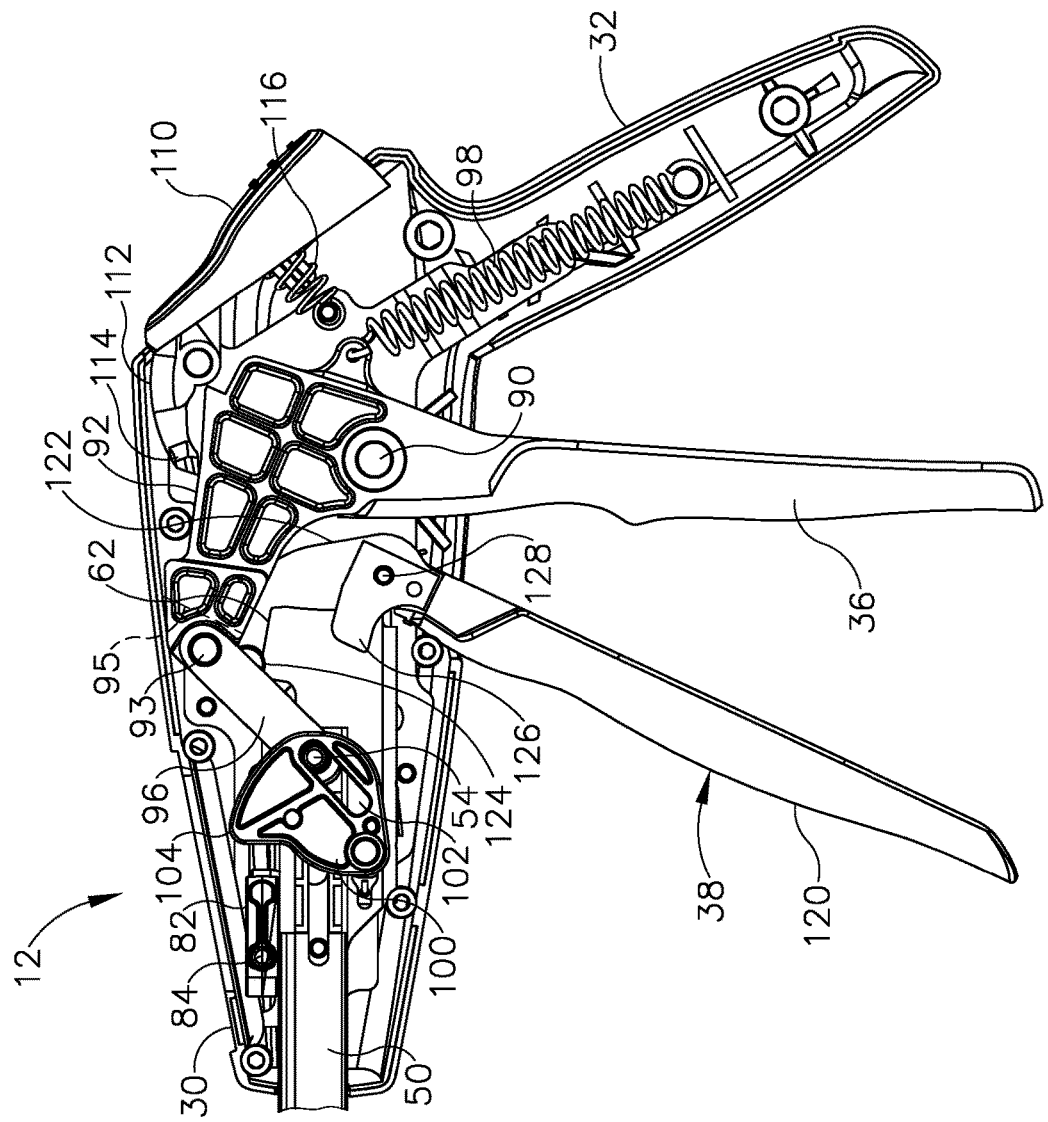
FIG. 4A depicts a side elevational view of the handle assembly of the surgical stapler of FIG. 1A, with various components omitted for clarity, showing the tissue retaining pin actuation system in an extended position to retain tissue while the closure system and the firing system are in unactuated states.
Figure 4B:
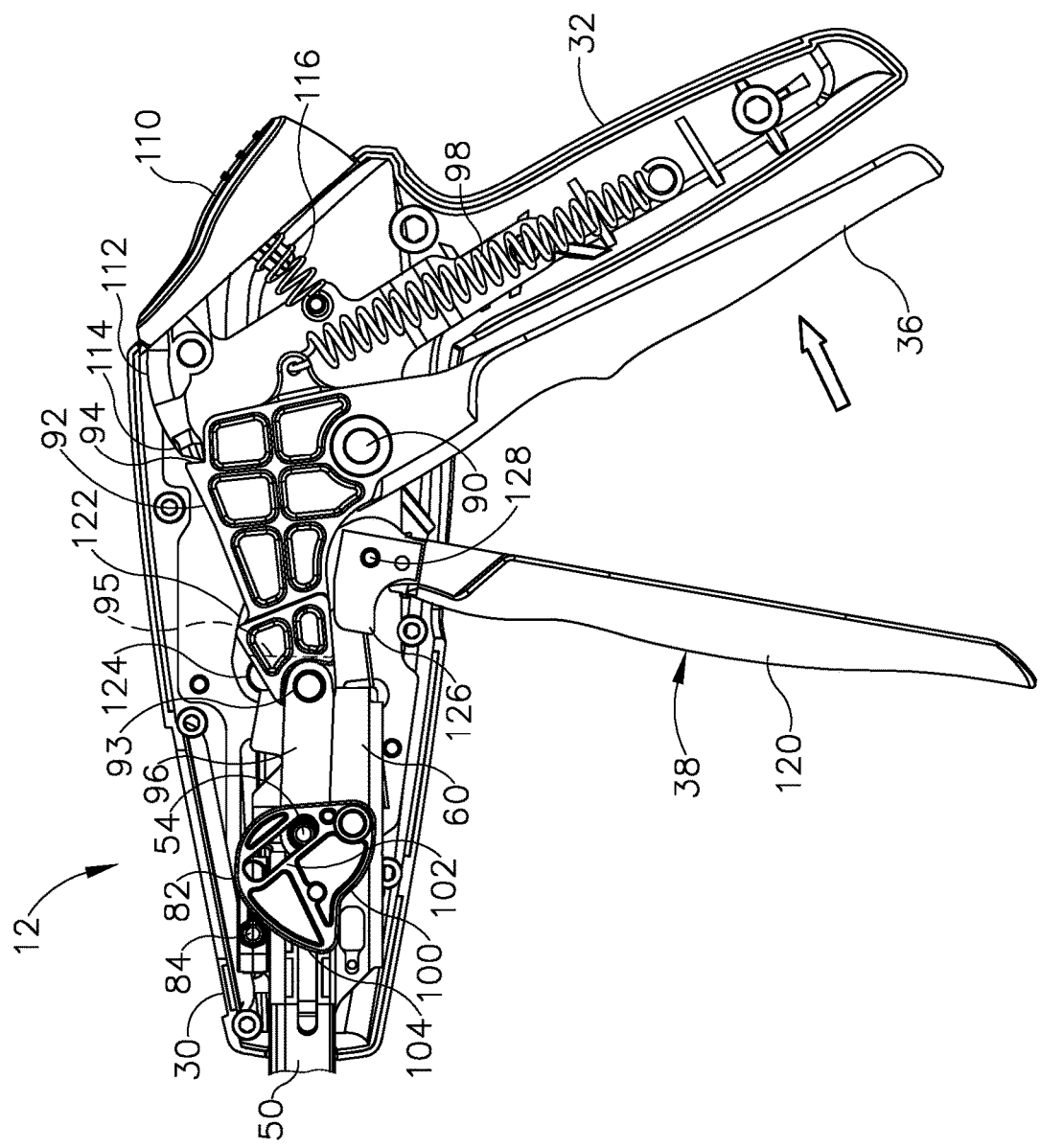
FIG. 4B depicts a side elevational view of the handle assembly of the surgical stapler of FIG. 1A, with various components omitted for clarity, showing the closure system actuated via a closure trigger to close the end effector and thereby clamp tissue.

As shown in FIGS. 4A-4B, pivoting of closure trigger (36) toward pistol grip (32) pivots advances closure trigger upper arm (92) distally and downwardly, thereby driving closure bar (50) distally via closure links (96). In turn, cartridge-receiving distal portion (52) of closure bar (50) drives cartridge housing (162) distally toward anvil (210). In this manner, end effector (16) is actuated from an open state (FIGS. 1A-1B) in which tissue is positionable within end effector (16), to a closed state (FIG. 1C) in which the tissue is clamped between cartridge housing (162) and anvil (210). A closure return spring (98) housed within pistol grip (32) of handle assembly (12) resiliently biases closure trigger (36) toward the unactuated state, and thus end effector (16) toward the open state.

In the present version, closure bar (50) is further configured to cooperate with tissue retaining pin actuation system (20) to automatically actuate retaining pin (176) distally to its extended position when an operator squeezes closure trigger (36). In that regard, as shown best in FIGS. 4A-4B, handle assembly (12) further includes a pair of camming yokes (100) rotatably disposed along the outer sides of closure links (96). Each camming yoke (100) includes an angled slot (102) that slidably receives a respective proximal post (54) of closure bar (50). As closure trigger (36) is actuated toward pistol grip (32), proximal posts (54) rotatably drive camming yokes (100) distally such that cam lobes (104) of yokes (100) engage corresponding side posts (84) of pushrod driver (82), thereby actuating pushrod (80) and thus tissue retaining pin (176) distally. Such automatic extension of tissue retaining pin (176) during closure of end effector (16) may be useful in the event that the operator does not manually actuate retaining pin (176) distally via slide (34) prior to actuating closure trigger (36).

Closure system (22) of the present example is further configured to releasably lock closure trigger (36) in the actuated position to provide effective clamping of tissue with end effector (16) without having to continuously squeeze closure trigger (36). As shown best in FIGS. 4A-4B, a release button (110) is pivotably disposed at a proximal end of handle assembly (12). A locking pawl (112) extends distally from an upper end of release button (110) and includes a pawl lug (114) that is resiliently biased into contact with an upper end of closure trigger upper arm (92), via a release button spring (116). Accordingly, pawl lug (114) is configured to slide along an upper surface of closure trigger upper arm (92) as closure trigger (36) is squeezed toward pistol grip (32). As shown in FIG. 4B, upon closure trigger (36) reaching a fully actuated position, pawl lug (114) drops into a proximal upper notch (94) of closure trigger upper arm (92), thereby locking closure trigger (36) in the fully actuated position. Should the operator wish to then reopen end effector (16), for example to reposition tissue within end effector (16) or otherwise release tissue once firing is complete, the operator may depress release button (110) to disengage pawl lug (114) from closure trigger (36). Via the resilient bias provided by closure return spring (98), closure trigger (36) then returns to the unactuated state and end effector (16) returns to the open state, shown in FIGS. 1A and 4A.

Firing system (24) of surgical stapler (10) includes firing trigger (38) of handle assembly (12), staple bar (60), knife bar (70), and staple driver member (186) and knife member (194) of staple cartridge unit (160). Features of knife bar (70) and staple driver member (186) are described in greater detail below in connection with FIG. 8. As shown in FIGS. 2 and 4A, firing trigger (38) of the present example is configured as an assembly having a lower shroud (120) that extends downwardly from handle housing (30) and is engageable by an operator; a pair of plates having arcuate upper arms (122) that extend upwardly and distally from lower shroud (120) and are positioned with handle housing (30); a rotatable cam pin (124) extending laterally between the free distal upper ends of arcuate upper arms (122); and a firing lockout projection (126) extending distally from the lower ends of arcuate upper arms (122) within handle housing (30). Cam pin (124) may be configured and operable in accordance with any of the teachings of U.S. patent application Ser. No. 16/395,359, entitled "Cartridge Based Lockout Mechanism for Right Angle Surgical Stapler," filed on Apr. 26, 2019, published as U.S. Pat. No. 2020/0337700 on Oct. 29, 2020, the disclosure of which is incorporated by reference herein.

Firing trigger (38) is pivotably coupled with handle housing (30) via a laterally extending pivot pin (128). Additionally, firing trigger (38) is positioned distal to closure trigger (36) such that arcuate upper arms (122) of firing trigger (38) are received into the slotted distal portion of closure trigger upper arm (92) as closure trigger (36) is actuated toward pistol grip (32). As shown in FIGS. 4A-4B, as the operator squeezes closure trigger (36) fully toward pistol grip (32), distally facing ledges (95) disposed within the distal slotted portion of closure trigger upper arm (92) engage cam pin (124) of firing trigger (38) and drive cam pin (124) distally by an initial amount. This causes the lower end of firing trigger (38) to pivot partially toward pistol grip (32) simultaneously with closure trigger (36), as shown in FIG. 4B.

Figure 4C:
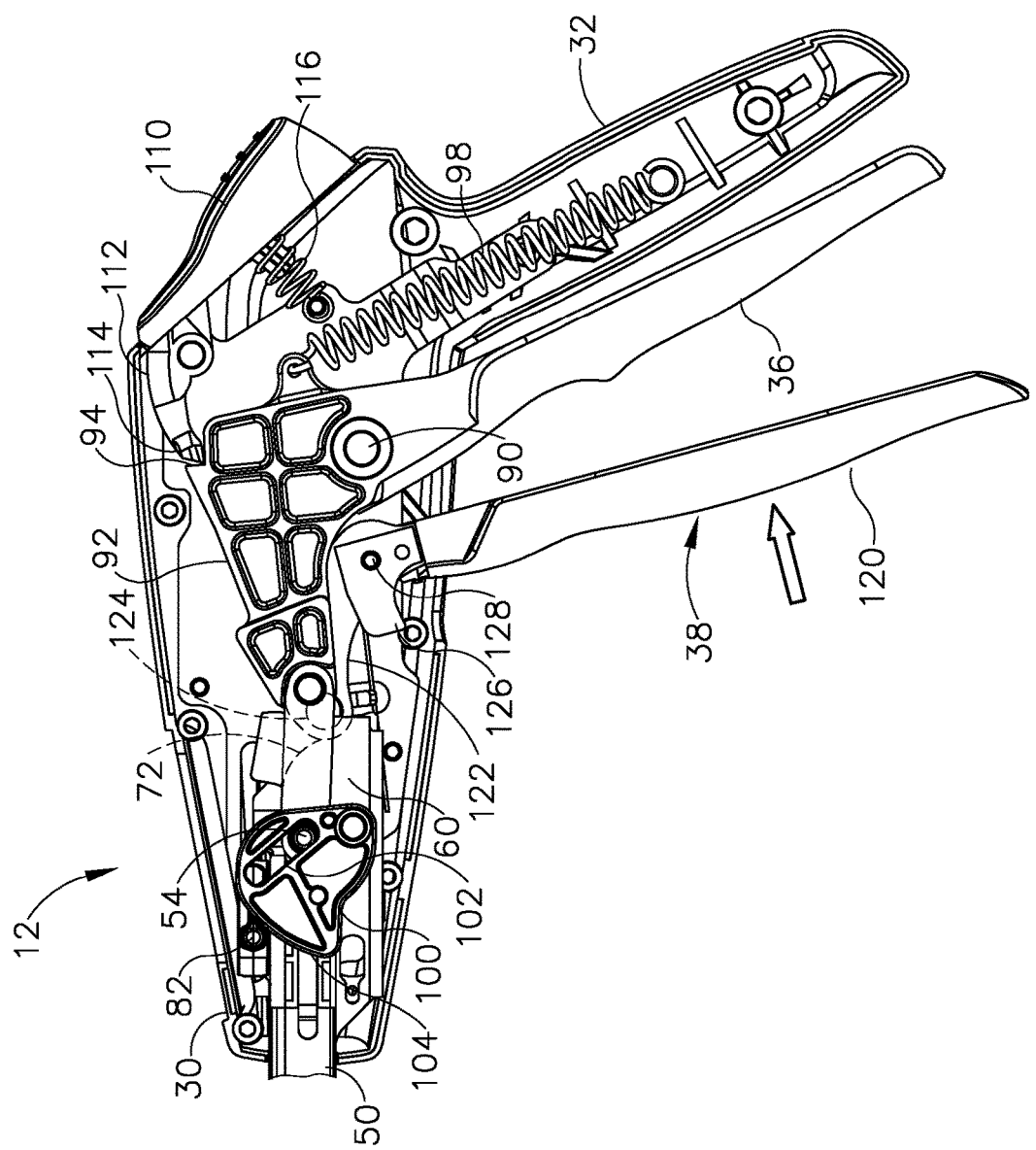
FIG. 4C depicts a side elevational view of the handle assembly of the surgical stapler of FIG. 1A, with various components omitted for clarity, showing the firing system actuated via a firing trigger to fire the end effector and thereby staple and cut tissue while the end effector remains in the closed state.
Figure 5:
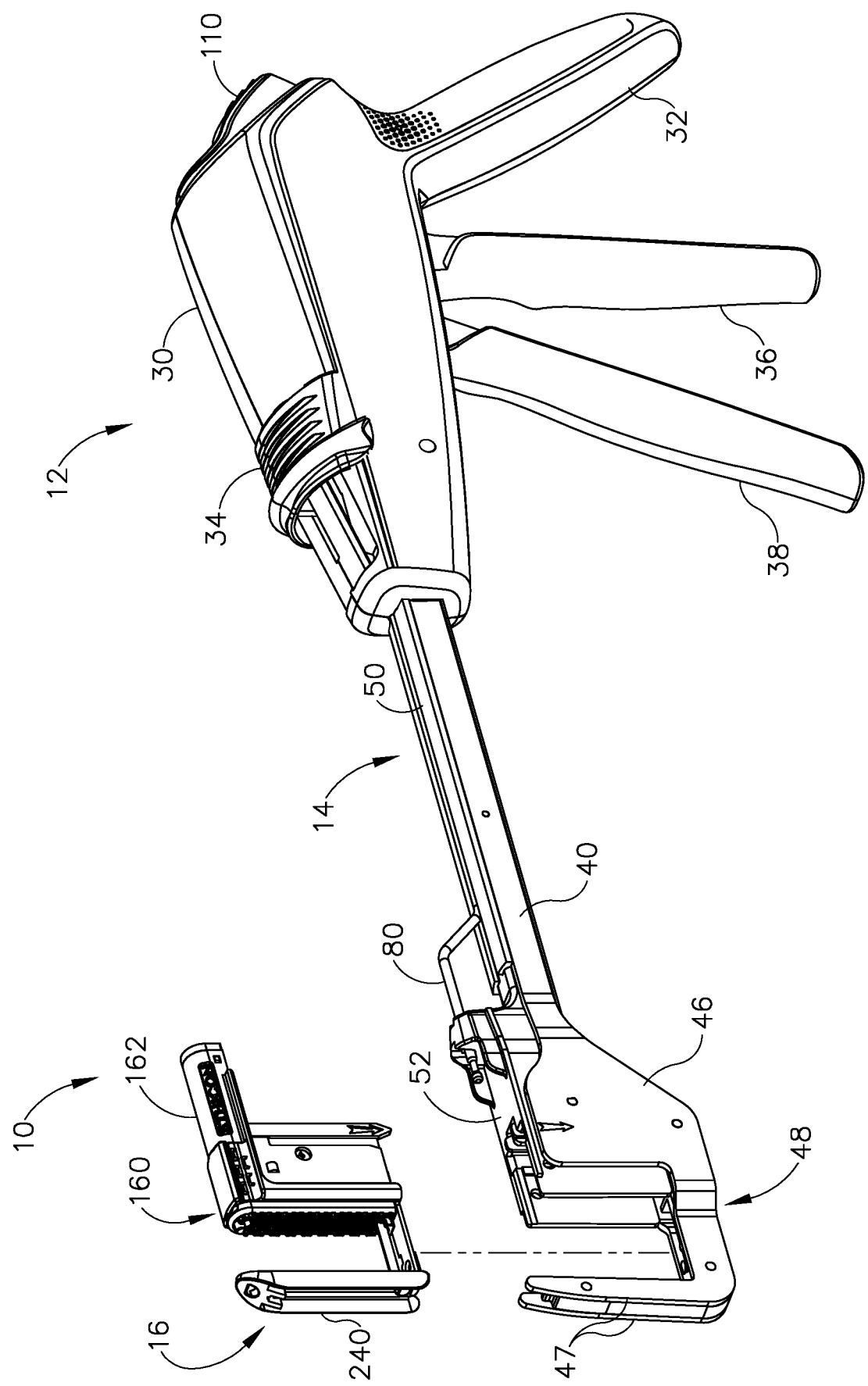
FIG. 5 depicts a perspective view of the surgical stapler of FIG. 1A, showing a staple cartridge unit of the end effector separated from a distal support structure of the end effector.

As shown in FIG. 4C, once end effector (16) has reached the fully closed state, further actuation of firing trigger (38) toward pistol grip (32) operates to "fire" end effector (16). In particular, outer portions of cam pin (124) engage proximal edges (62) of staple bar (60), thus driving staple bar (60) distally relative to closure bar (50). As described in greater detail below in connection with FIGS. 12A-12D, distal edges (64) of staple bar (60) engage a proximal end of staple driver member (186) within staple cartridge housing (162), thus driving staple driver member (186) distally through staple cartridge housing (162) to drive staples into tissue clamped by end effector (16). Actuation of firing trigger (38) toward its fully actuated state also causes a medial portion of cam pin (124), disposed between arcuate upper arms (122) of firing trigger (38), to engage a rounded proximal edge (72) of knife bar (70), thus driving knife bar (70) distally relative to closure bar (50). As described in greater detail below in connection with FIGS. 12A-12D, a distal edge (74) of knife bar (70) engages a proximal end of knife member (194) within staple cartridge housing (162), thus driving knife member (194) distally through staple driver member (186) to cut the tissue clamped by end effector (16).

Firing system (24) of the present example is suitably configured such that staple bar (60) and knife bar (70) translate distally together as firing trigger (38) is actuated through a primary range of motion toward pistol grip (32); and such that knife bar (70) continues to translate distally relative to staple bar (60) as firing trigger (38) is further actuated through a final range of motion toward pistol grip (32). Advantageously, such a configuration ensures that the tissue clamped by end effector (16) is fully stapled and that proper hemostasis is thus achieved along the intended tissue cut line before the tissue is cut by knife member (194).

As shown in FIG. 2, firing system (24) further includes a knife return spring (130) housed within handle assembly (12). Knife return spring (130) is anchored at its distal end to the distal end of knife bar (70), and at its proximal end to the distal end of closure bar (50). Accordingly, knife return spring (130) is operable to resiliently bias knife bar (70) proximally relative to closure bar (50) and staple bar (60) when firing trigger (38) is released. As shown in FIGS. 3 and 12A-12D, knife bar (70) includes a distal hook (76) that is captured by knife member (194) to thereby secure knife member (194) axially to knife bar (70). Accordingly, when the operator releases firing trigger (38) after completing a firing stroke, knife bar (70) and knife member (194) automatically retract proximally to safely house a distal cutting edge (200) of knife member (194) within staple cartridge housing (162).

As shown in FIG. 2, surgical stapler (10) of the present example further includes a proximal firing lockout mechanism in the form of a pivotable lever (140), which is operable to inhibit actuation of firing trigger (38) until end effector (16) has been fully closed by closure trigger (36). Firing lockout lever (140) is housed within handle assembly (12) and is pivotably mounted to an outer side of the proximal frame portion (42) of the left side plate (40). Firing lockout lever (140) is resiliently biased by a spring (146) toward a position in which a lower tab (142) of proximal lockout lever (140) blocks downward movement of firing lockout projection (126) of firing trigger (38), thus inhibiting actuation of firing trigger (38) when closure trigger (36) has not been fully actuated to close end effector (16). When closure trigger (36) reaches a fully actuated state, an upper arm (144) of firing lockout lever (140) is driven downwardly by pawl lug (114) of release button (110), thus rotating lower tab (142) away from firing lockout projection (126) and permitting actuation of firing trigger (38). Firing lockout lever (140) and exemplary variations thereof are described in greater detail below.

Though not shown, shaft assembly (14) of surgical stapler (10) may include various additional components, such as an articulating joint, or may include a rearrangement of various components such that shaft assembly (14) may be modular relative to handle assembly (12).

B. End Effector of Surgical Stapler

End effector (16) of surgical stapler (10) includes distal support structure (48) defined by distal portions of side plates (40), cartridge-receiving distal portion (52) of closure bar (50), distal portions of staple bar (60) and knife bar (70), and replaceable staple cartridge unit (160). As shown best in FIGS. 5-8, staple cartridge unit (160) of the present version includes cartridge housing (162) and anvil (210) spaced apart from one another so as to define an axial gap (G) therebetween for receiving patient tissue to be stapled and cut. Cartridge housing (162) includes a distally facing deck (164) that is configured to clamp tissue against anvil (210) and extends transversely to a longitudinal axis of shaft assembly (14), along with anvil (210), thus providing end effector (16) with a "right angle" configuration.

Cartridge deck (164) includes an elongate linear knife slot (166) configured to slidably receive a knife (198) therethrough, and a plurality of staple openings (168) arranged in linear rows along either side of elongate linear knife slot (166) and configured to house a plurality of unformed staples (170) therein. Deck (164) of the present example further includes a plurality of stand-off features (172) interposed with staple openings (168) and configured to optimize grip and compression of patient tissue as the tissue is clamped between deck (164) and anvil (210). Deck (164) may be further configured in accordance with at least some of the teachings of U.S. patent application Ser. No. 16/234,740, entitled "Surgical Stapler with Sloped Staple Deck for Varying Tissue Compression," filed Jan. 14, 2019, published as U.S. Pat. No. 2020/0205811 on Jul. 2, 2020, the disclosure of which is incorporated by reference herein.

An elongate upper body portion (174) of cartridge housing (162) slidably houses tissue retaining pin (176) and a couplet (180) secured to a proximal end of tissue retaining pin (176). Couplet (180) is configured to releasably couple tissue retaining pin (176) with a distal end of pushrod (80) of tissue retaining pin actuation system (20) when staple cartridge unit (160) is seated within distal support structure (48) of end effector (16). An end cap member (182) secured to a proximal end of upper body portion (174) is configured to constrain tissue retaining pin (176) and couplet (180) proximally within cartridge housing (162), while permitting tissue retaining pin (176) to translate between its proximal retracted position (see FIGS. 1A and 12A), and its distal extended position (see FIGS. 1B and 12B). Tissue retaining pin (176) includes a tapered distal tip (178) that is configured to pierce tissue as retaining pin (176) is extended toward anvil (210).

A lower body portion (184) of cartridge housing (162) slidably receives staple driver member (186) and knife member (194) therein. As shown best in FIG. 8, staple driver member (186) of the present version includes a base portion (188), a plurality of staple driver elements (190) projecting distally from base portion (188), and an interior channel (192) that extends axially through staple driver member (186) and is configured to slidably receive knife member (194). Each staple driver element (190) is configured to be slidably received within a respective staple opening (168) of cartridge housing (162) and drive a respective staple (170) from the opening (168) in response to actuation of closure trigger (36). While staple driver elements (190) of the present version are securely affixed to base portion (188), it will be appreciated that base portion (188) and staple driver elements (190) may be provided separately in other versions.

Knife member (194) includes a base portion (196) and a knife (198) secured to and extending distally from base portion (196) and having a distal cutting edge (200). Knife (198) is formed with a flat, plate-like shape that enables knife (198) to perform linear cuts on patient tissue. Knife member (194) is slidably received within interior channel (192) of staple driver member (186) such that knife (198) is configured to translate longitudinally through staple driver member (186) and elongate linear knife slot (166) of cartridge housing (162) for cutting tissue clamped by end effector (16) in response to full actuation of firing trigger (38).

Figure 8:
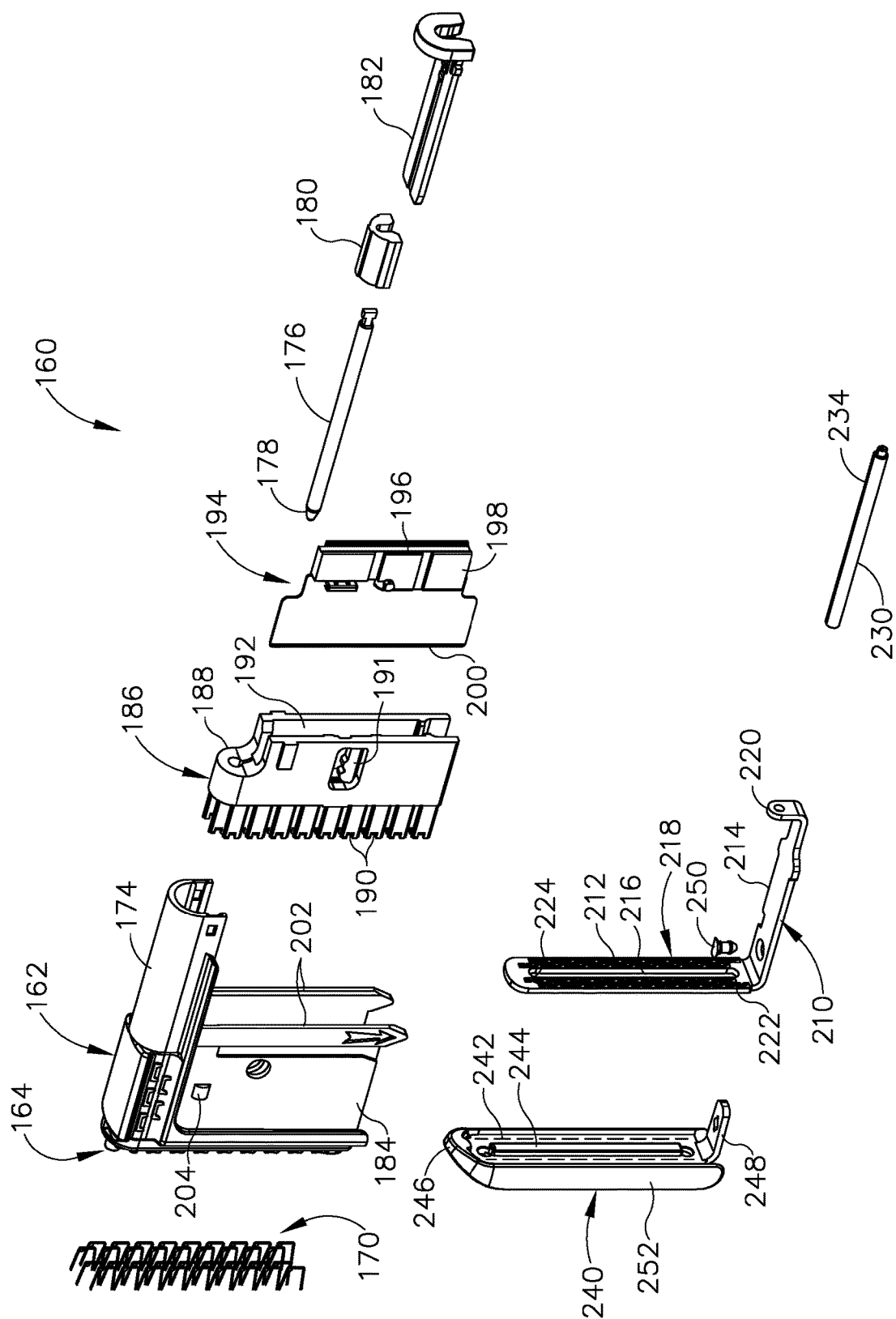
FIG. 8 depicts a disassembled perspective view of the staple cartridge unit of the surgical stapler of FIG. 1A.

As shown best in FIG. 8, anvil (210) of staple cartridge unit (160) includes a distal plate portion (212) and a coupling arm (214) extending proximally from a lower end of distal plate portion (212). Distal plate portion (212) is configured to cooperate with cartridge deck (164) to clamp tissue to be stapled and cut. Distal plate portion (212) includes an elongate linear slot (216) and a plurality of staple-forming pockets (218) arranged in linear rows along each side of slot (216). Pockets (218) are configured to receive and deform legs of staples (170) ejected from cartridge housing (162) for forming the staples (170) in tissue clamped between distal plate portion (212) and cartridge deck (164).

Figure 6:
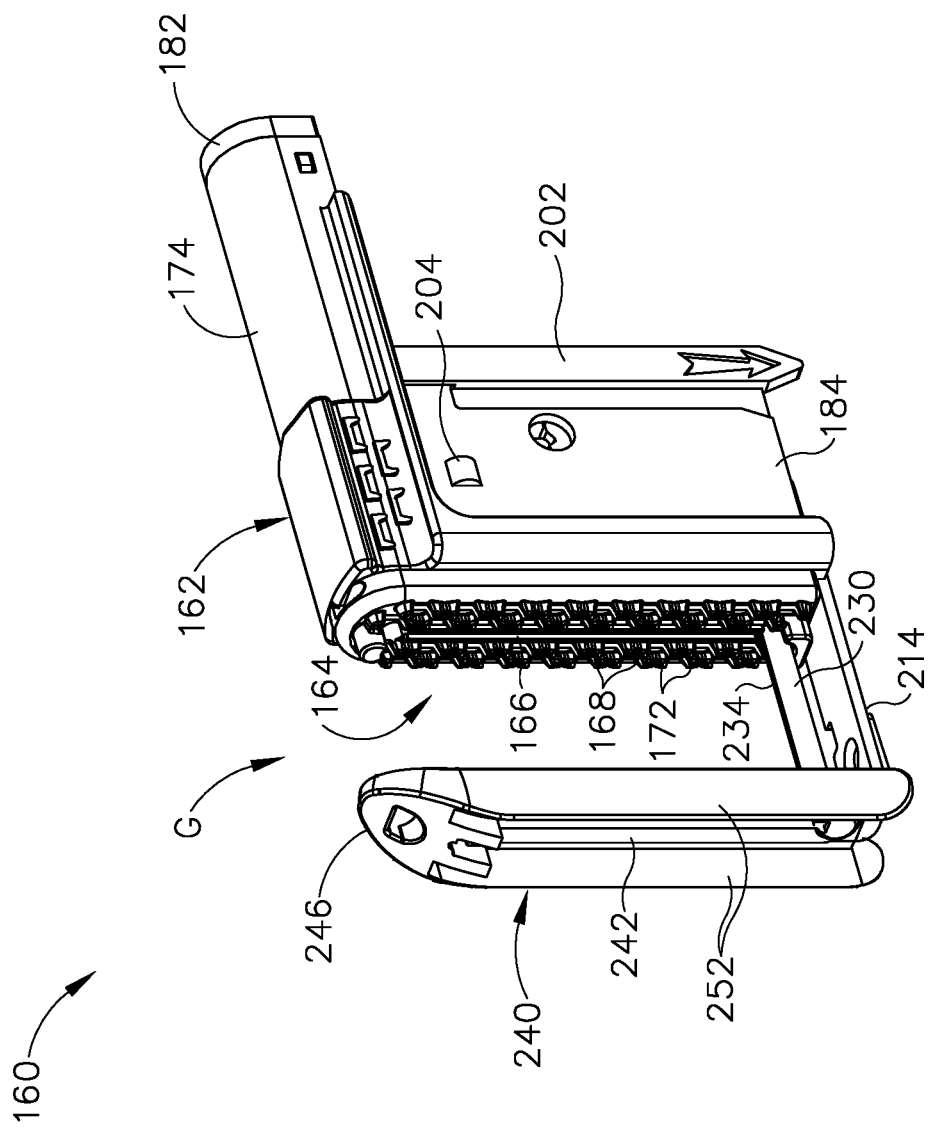
FIG. 6 depicts a distal left side perspective view of the staple cartridge unit of the surgical stapler of FIG. 1A.
Figure 7:
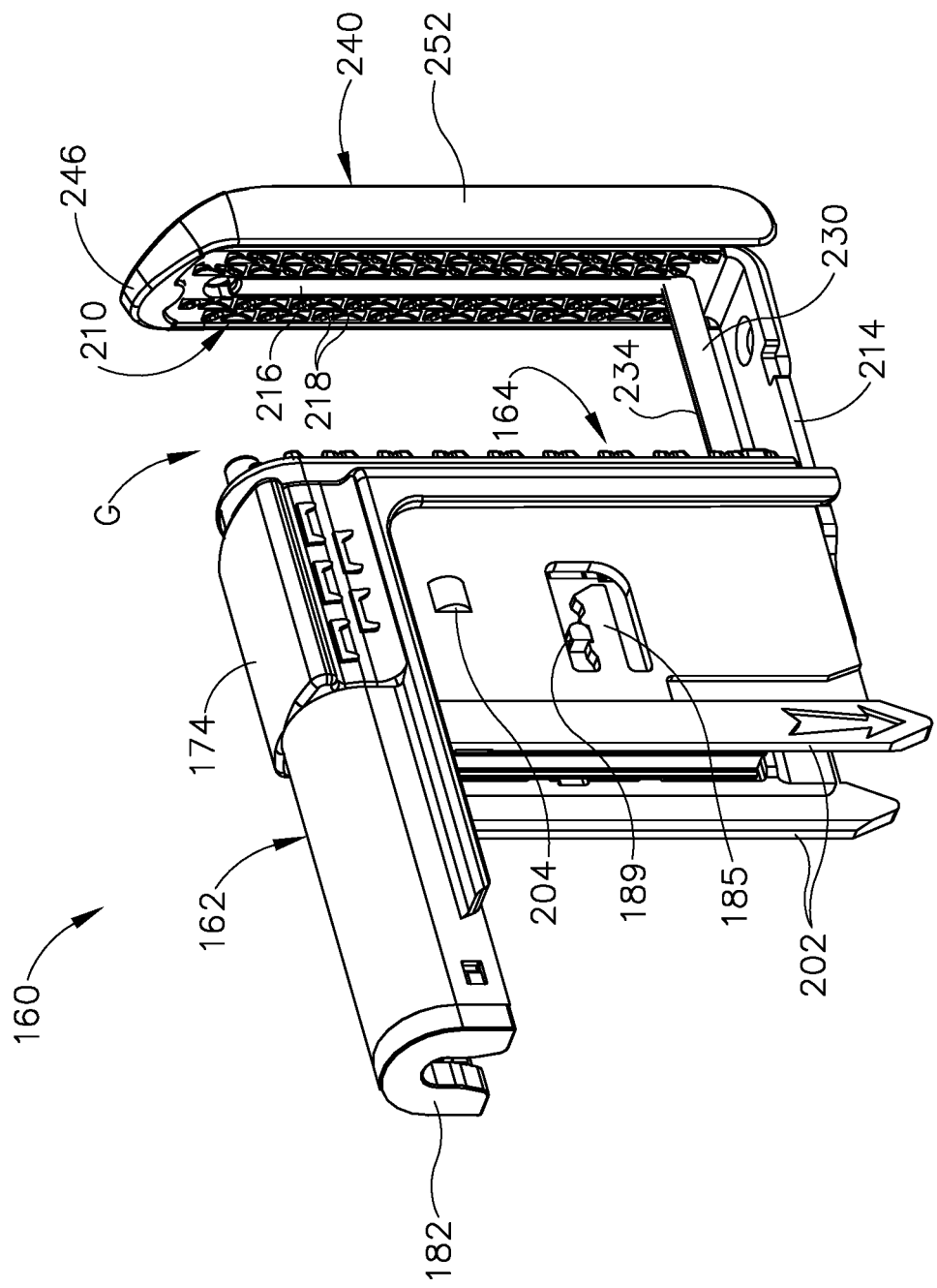
FIG. 7 depicts a proximal right side perspective view of the staple cartridge unit of the surgical stapler of FIG. 1A.
Figure 12A:
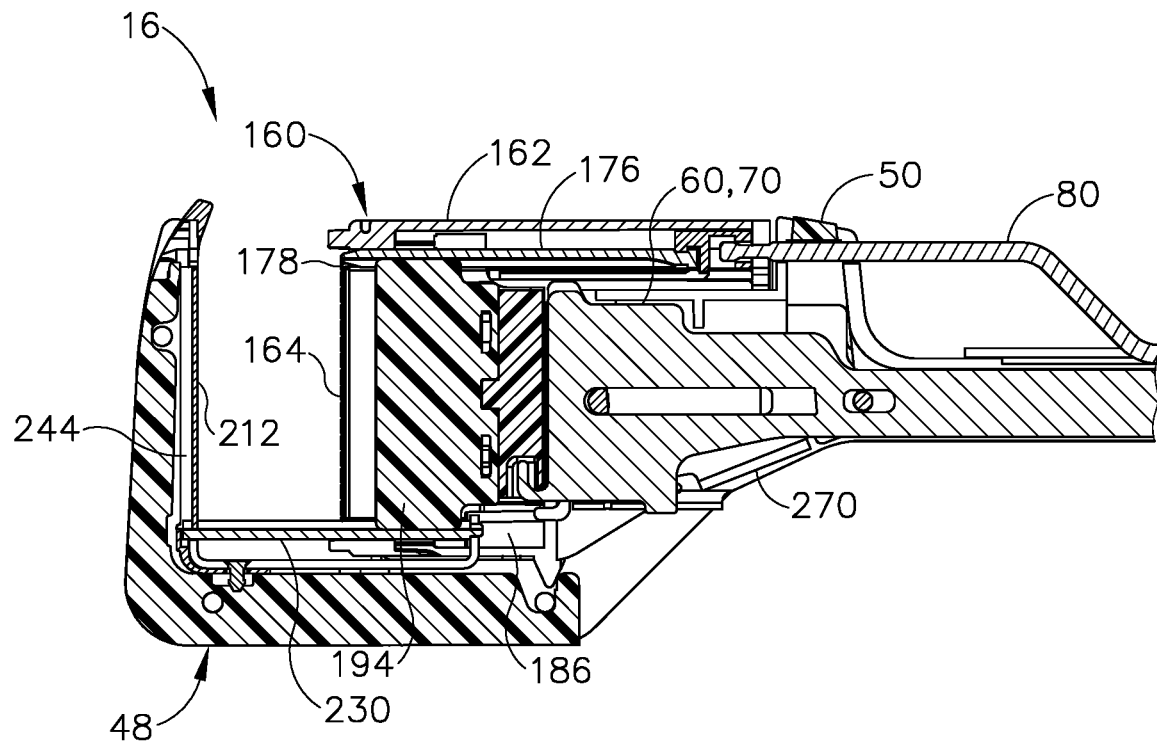
FIG. 12A depicts a side sectional view of the end effector of the surgical stapler of FIG. 1A, showing a tissue retaining pin in a retracted position while the end effector is in an open state.
Figure 12B:
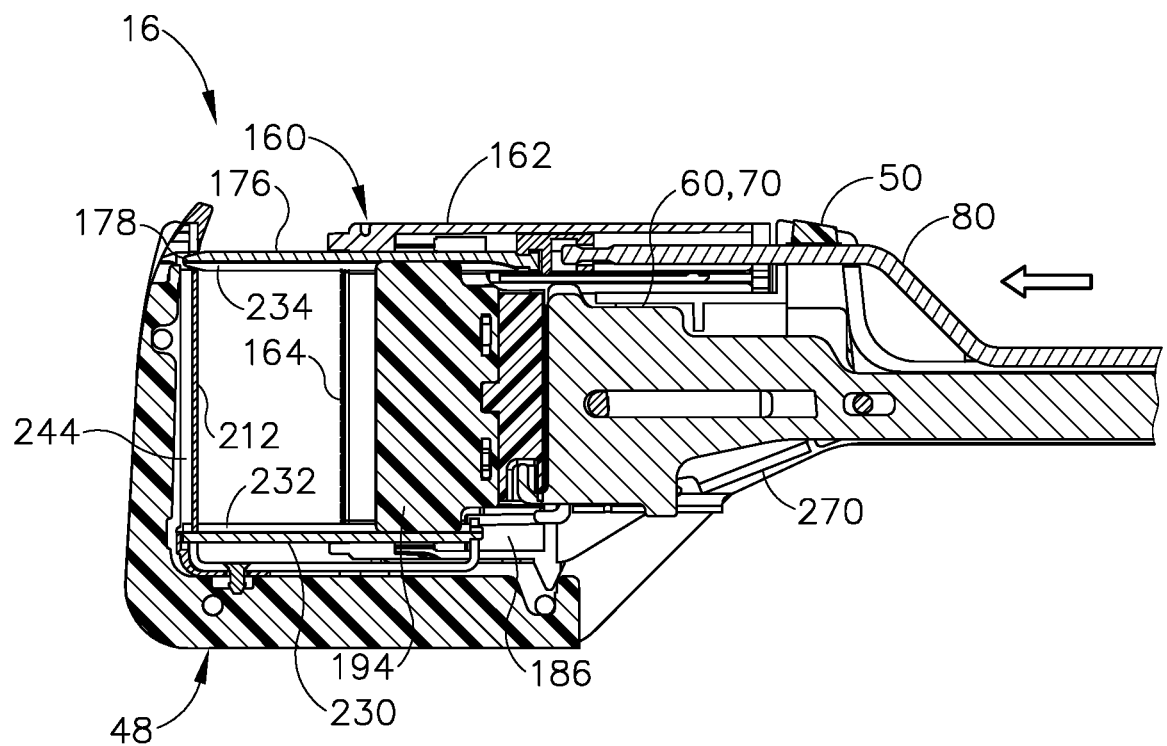
FIG. 12B depicts a side sectional view of the end effector of the surgical stapler of FIG. 1A, showing the tissue retaining pin in an extended position to retain tissue while the end effector remains in the open state.
Figure 12C:
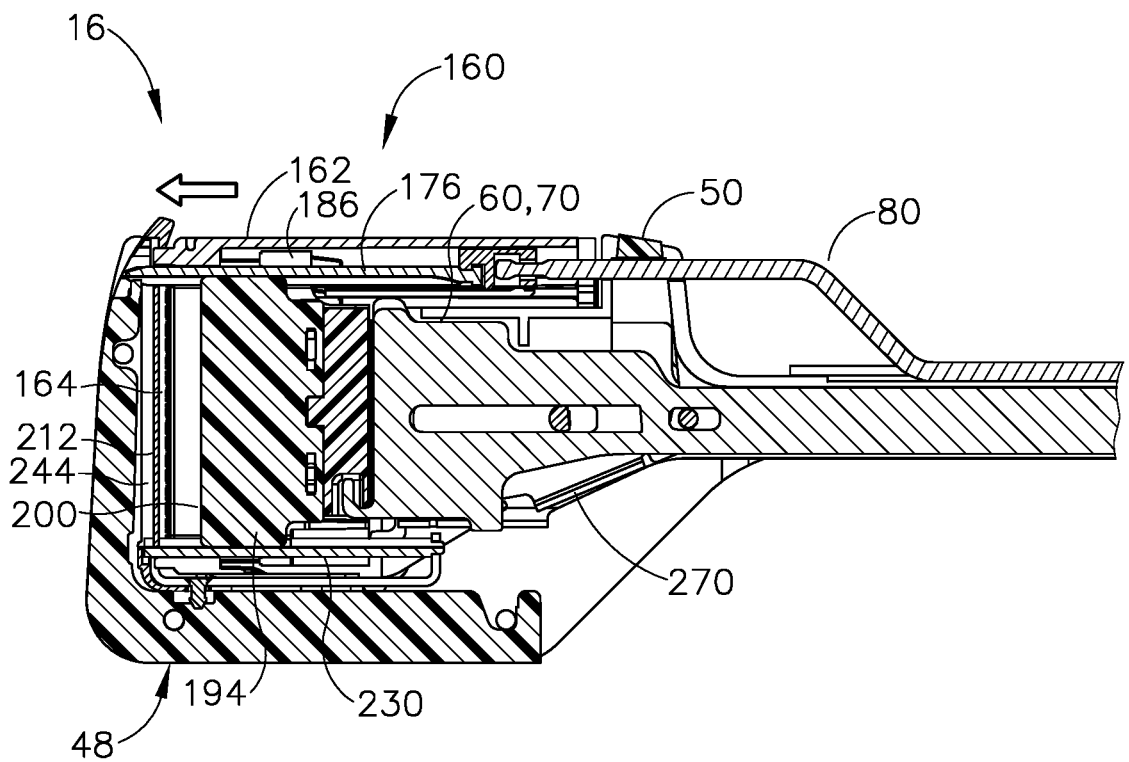
FIG. 12C depicts a side sectional view of the end effector of the surgical stapler of FIG. 1A, showing the end effector actuated to a closed state to clamp tissue while the tissue retaining pin remains in the extended position.

A guide pin (230) extends longitudinally between anvil plate portion (212) and cartridge housing (162) and is configured to guide longitudinal translation of cartridge housing (162) between the proximal open position (see FIGS. 1A and 12A) and the distal closed position (see FIGS. 1C and 12C). A proximal end of guide pin (230) is constrained by a proximal tab (220) of anvil coupling arm (214), shown in FIG. 8, and a distal end of guide pin (230) is constrained within a lower opening (222) formed in anvil plate portion (212). An upper opening (224) formed in anvil plate portion (212) is configured to receive and constrain tapered distal tip (178) of tissue retaining pin (176) in the extended position, such that tissue retaining pin (176) may cooperate with guide pin (230) to guide longitudinal translation of cartridge housing (162) relative to anvil (210). As seen in FIGS. 6-8, an inner side of guide pin (230) may include a longitudinal groove (232), which is configured to cooperate with a similar groove (234) (see FIGS. 12A-12D) to slidably guide knife (198) between retracted and extended positions relative to cartridge housing (162).

Staple cartridge unit (160) further includes a tissue cutting washer (240) fixed to anvil (210), and which is configured to cooperate with knife (198) to cut tissue clamped by end effector (16). As shown best in FIGS. 8 and 10-11, tissue cutting washer (240) includes an elongate, plate-like body (242) that extends along the distal side of anvil plate portion (212). Washer body (242) includes an elongate cutting element (244) that protrudes proximally through elongate slot (216) of anvil plate portion (212). Cutting element (244) functions as a cutting board by providing knife cutting edge (200) with a flat surface against which cutting edge (200) cuts tissue. At least cutting element (244) of tissue cutting washer (240) may comprise a polymeric material, such as high-density polyethylene (HDPE). In that regard, knife (198) may cut axially into cutting element (244), along its longitudinal centerline, when cutting tissue. While cutting element (244) of the present version provides a generally planar cutting surface, it will be appreciated that cutting element (244) may be alternatively configured in other versions.

Tissue cutting washer (240) further includes a rounded tip (246) at an upper end of washer body (242), and a coupling arm (248) extending proximally from a lower end of washer body (242). Washer tip (246) captures and thereby constrains an upper end of anvil plate portion (212), and its rounded configuration promotes atraumatic interaction with patient tissue. A press-fit pin (250) is configured to be inserted through openings formed in proximal coupling arms (214, 248) of anvil (210) and tissue cutting washer (240), thereby securely coupling anvil (210) and cutting washer (240) together.

Figure 10:
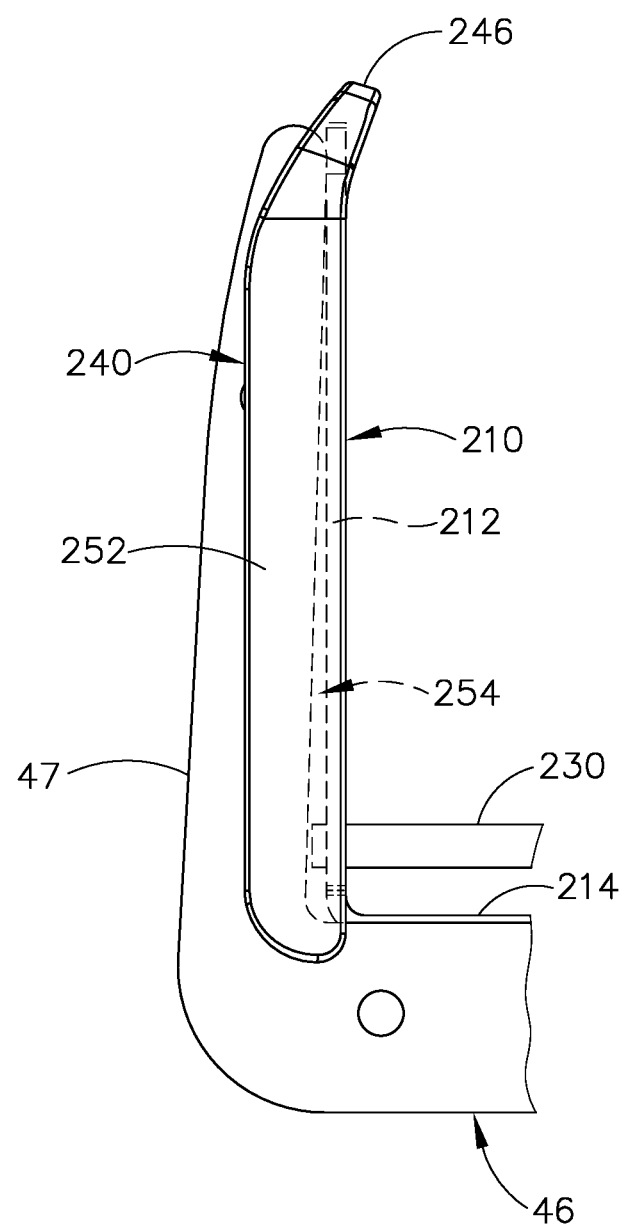
FIG. 10 depicts a side elevational view of a distal portion of the end effector of the surgical stapler of FIG. 1A following insertion of the staple cartridge unit into the distal support structure.
Figure 11:
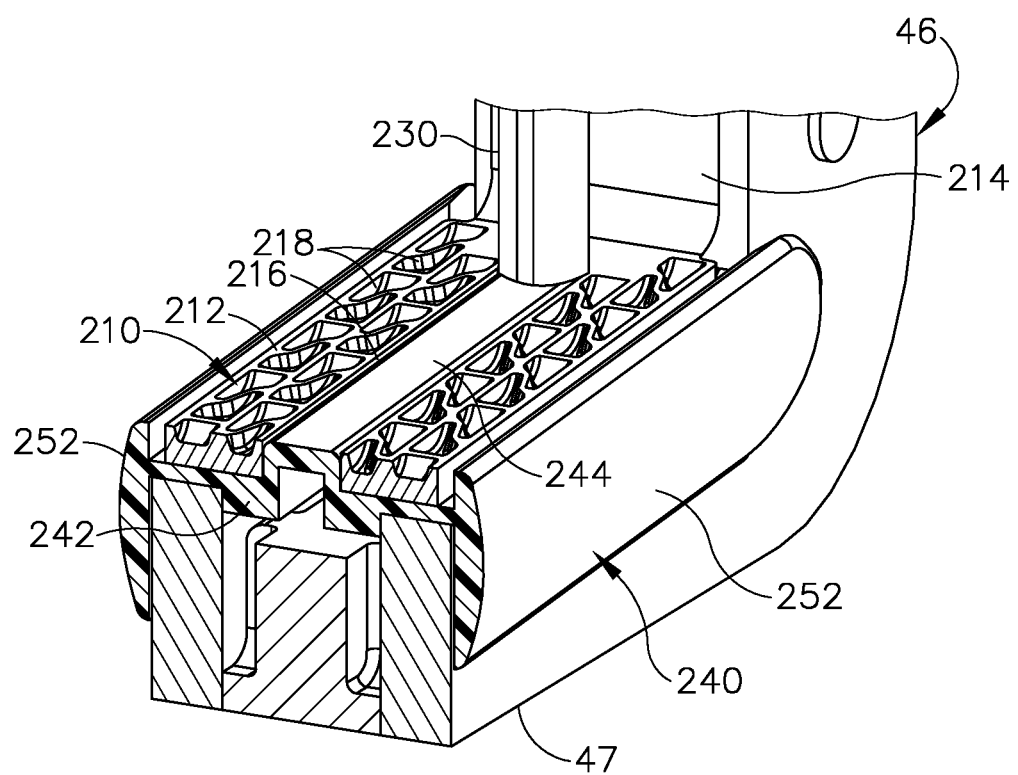
FIG. 11 depicts a sectional view of the distal portion of the end effector of the surgical stapler of FIG. 1A, showing interaction of a tissue cutting washer of the staple cartridge unit with the distal support structure.

Tissue cutting washer (240) further includes a pair of side flanges (252) that extend along a full length of anvil plate portion (212). As shown in FIGS. 10 and 11, each side flange (252) extends proximally to cover a respective side edge of anvil plate portion (212), and distally to cover at least a portion of distal hook (47) of the respective side plate (40) defining distal support structure (48). Accordingly, and advantageously, side flanges (252) function to cover an axial gap (254) that may form between anvil plate portion (212) and distal hooks (47), thereby preventing tissue from entering into and getting pinched within axial gap (254) in a manner that might otherwise result in undesirable trauma to the tissue. As shown in FIG. 11, the outer surfaces of side flanges (252) may be rounded to further enhance the atraumatic characteristics of the outer periphery of tissue cutting washer (240). Tissue cutting washer (240) may be further configured and operable in accordance with any of the teachings of U.S. patent application Ser.No. 16/395,357, entitled "Tissue Cutting Washer for Right Angle Surgical Stapler," filed on Apr. 26, 2019, published as U.S. Pub. No. 2020/0337698 on Oct. 29, 2020, the disclosure of which is incorporated by reference herein.

Figure 9B:
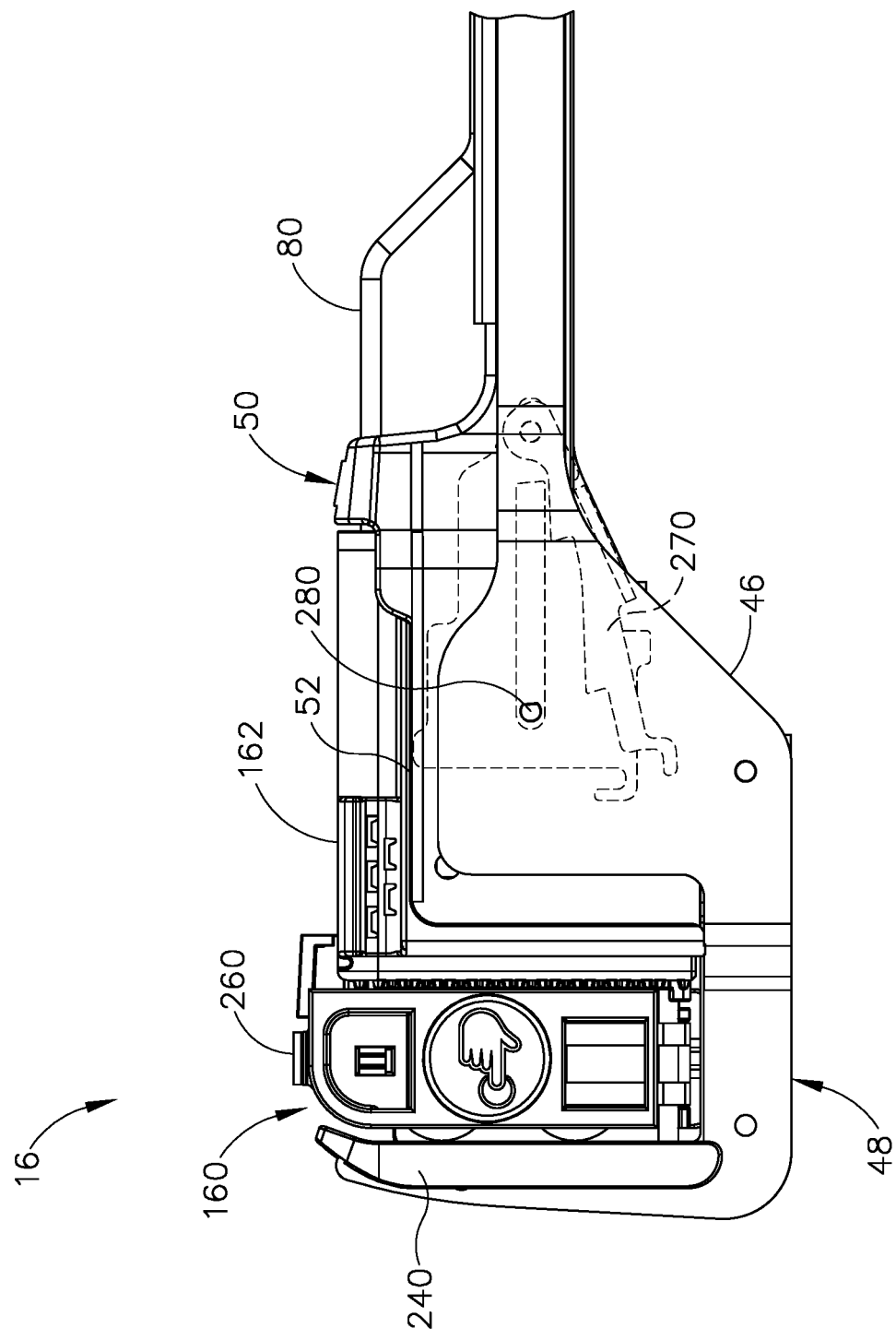
FIG. 9B depicts a side elevational view of the end effector of the surgical stapler of FIG. 1A, showing the lockout member in a bypass position when an unspent staple cartridge unit is seated within the distal support structure.

C. Exemplary Loading of Staple Cartridge Unit into Distal Support Structure of End Effector FIGS. 9A and 9B show loading of staple cartridge unit (160) in its unused (or "unspent") state into distal support structure (48) of end effector (16). As shown in FIG. 9A, and as described briefly above, distal support structure (48) is configured with a U-shaped side profile having a distal side defined by distal hooks (47), a proximal side defined by a proximal portion of distal jaw portion (46) and a distal end of cartridge-receiving distal portion (52) of closure bar (50), and an upwardly opening axial gap disposed therebetween.

Staple cartridge unit (160) is shown in FIGS. 9A-9B provided with a staple retainer (260) that is removably positioned between deck (164) and anvil plate portion (212) to retain staples (170) within staple openings (168), and to ensure proper axial spacing between deck (164) and anvil plate portion (212) as staple cartridge unit (160) is inserted into distal support structure (48). Staple retainer (260) may be configured and operable in accordance with any of the teachings of U.S. patent application Ser. No. 16/395,364, entitled "Staple Retainer for Right Angle Surgical Stapler," filed on Apr. 26, 2019, published as U.S. Pub. No. 2020/0337701 on Oct. 29, 2020, issued as U.S. Pat. No. 11,166,721 on Nov. 9, 2021, the disclosure of which is incorporated by reference herein. Upon removal of staple retainer (260), staple cartridge unit (160) presents a U-shaped side profile similar to that of distal support structure (48), with a distal side defined by anvil plate portion (212) and tissue cutting washer (240), a proximal side defined by cartridge deck (164), and upwardly opening axial gap (G) disposed therebetween.

As shown in FIG. 9A, the user first aligns proximal side rails (202) formed on lower body portion (184) of cartridge housing (162) with inner channels (56) formed in cartridge-receiving distal portion (52) of closure bar (50) (see FIG. 3). As shown in FIG. 9B, the user then presses staple cartridge unit (160) downwardly into distal support structure (48) of end effector (16) such that proximal side rails (202) of cartridge housing (162) slide downwardly into inner channels (56) of closure bar (50), and such that distal hooks (47) of side plates (40) slide into grooves formed in the distal side of tissue cutting washer body (242) (see FIG. 11). As staple cartridge unit (160) fully seats within distal support structure (48), detent protrusions (204) formed on lower body portion (184) of cartridge housing (162) are receiving within respective openings (58) formed in cartridge-receiving distal portion (52) of closure bar (50), thereby removably securing staple cartridge unit (160) within distal support structure (48). Engagement of cartridge detent protrusions (204) with openings (58) may provide the user with tactile and/or audible feedback to confirm that staple cartridge unit (160) has been fully seated within distal support structure (48).

As shown in FIG. 9A, a distal lockout lever (270) is pivotably coupled to a distal end of staple bar (60). Distal lockout lever (270) extends distally toward distal edges (64) of staple bar (60) and knife bar (70) and is configured to releasably engage a fixed distal pin (280) that extends laterally through distal portions of side plates (40), closure bar (50), staple bar (60), and knife bar (70). Distal lockout lever (270) is resiliently biased toward a raised position shown in FIG. 9A and is pivotable toward a lowered position shown in FIG. 9B in response to engagement by a proximal end of staple driver member (186) upon insertion of an unspent staple cartridge unit (160) into distal support structure (48). In the raised position, distal lockout lever (270) lockingly engages fixed distal pin (280) and thereby inhibits distal actuation of staple bar (60) and knife bar (70), and thus firing of staple cartridge unit (160). In the lowered position, distal lockout lever (270) disengages fixed distal pin (280) and thus permits distal actuation of staple bar (60) and knife bar (70) for firing of staple cartridge unit (160). Distal lockout lever (270) and other lockout features of surgical stapler (10) may be further configured and operable in accordance with any of the teachings of U.S. patent application Ser. No. 16/395,359, entitled "Cartridge Based Lockout Mechanism for Right Angle Surgical Stapler," filed on Apr. 26, 2019, published as U.S. Pub. No. 2020/0337700 on Oct. 29, 2020, incorporated by reference above.

D. Exemplary Actuation of Surgical Stapler

Having described various structural features of surgical stapler (10) above, including staple cartridge unit (160), exemplary actuation of surgical stapler (10) during a surgical procedure will now be described below. After loading an unspent staple cartridge unit (160) into distal support structure (48) in the manner described above, end effector (16) is then suitably manipulated within a body cavity of a patient to position patient tissue within staple cartridge gap (G), between anvil plate portion (212) and cartridge deck (164). As shown in FIGS. 12A and 12B, pushrod (80) is then actuated distally via slide (34) to drive pushrod (80) distally, thereby extending tissue retaining pin (176) from cartridge housing (162) so that its distal tip (178) pierces through any tissue overlying the upper end of cartridge deck (164) and seats within the upper end of anvil plate portion (212). In this manner, the patient tissue is securely retained within cartridge gap (G) before closure.

As shown in FIG. 12C, closure bar (50) is then actuated distally via closure trigger (36), thereby driving cartridge housing (162) distally along guide pin (230) and tissue retaining pin (176) to clamp tissue between cartridge deck (164) and anvil plate portion (212). As shown in the present example, staple bar (60) and knife bar (70) actuate distally with closure bar (50) and cartridge housing (162) so that staple driver member (186) and knife member (194) are suitably positioned for firing upon full closure of end effector (16). As described above, end effector (16) is releasably maintained in the fully closed state by locking pawl (112) of release button (110) of handle assembly (12).

Figure 12D:
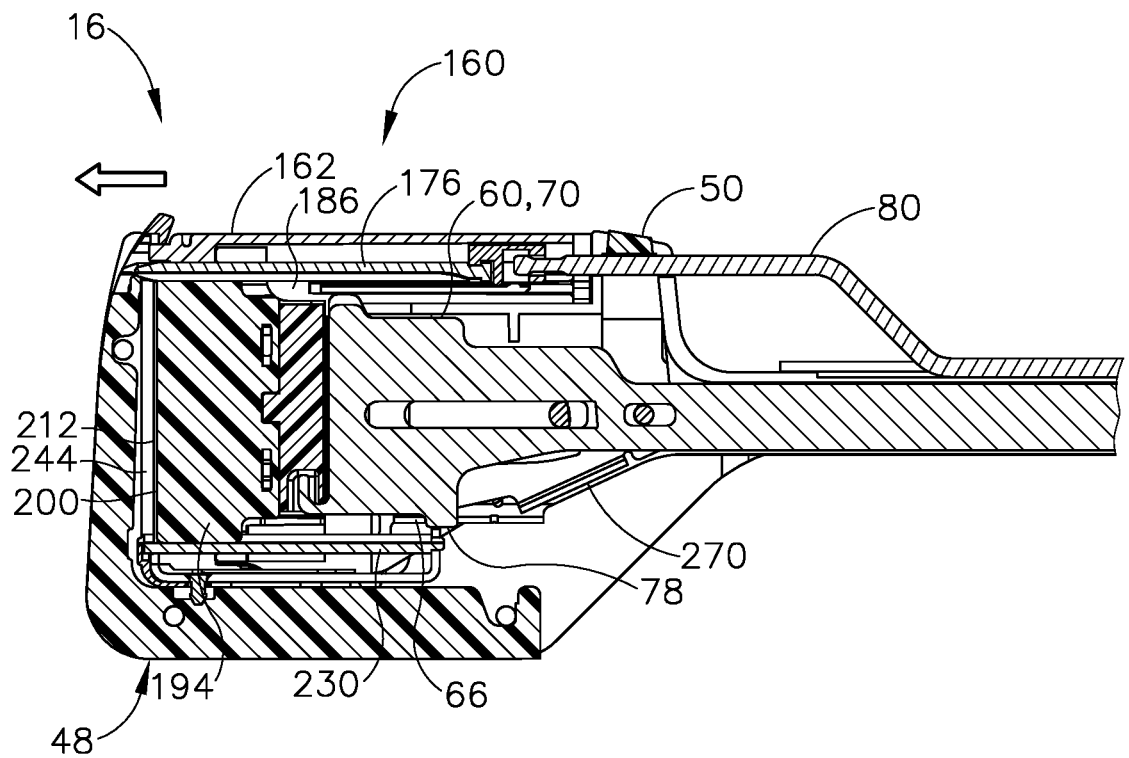
FIG. 12D depicts a side sectional view of the end effector of the surgical stapler of FIG. 1A, showing the end effector further actuated to a fired state to staple and cut tissue while remaining in the closed state.

As shown in FIG. 12D, staple bar (60) and knife bar (70) are then actuated distally via firing trigger (38), thereby driving staple driver member (186) and knife bar (70) distally through cartridge housing (162). Staple driver elements (190) of staple driver member (186) advance distally through staple openings (168), thereby driving staples (170) housed therein distally through the clamped tissue and into staple-forming pockets (218) of anvil plate portion (212), such that the staples (170) are formed in the tissue. Knife member (194) drives knife (198) distally through elongate knife slot (166) of cartridge deck (164), through the clamped tissue, and against cutting element (244) of tissue cutting washer (240), thereby severing the clamped tissue along a linear cut line between the innermost rows of formed staples (170). Upon cutting fully through the clamped tissue, knife cutting edge (200) may penetrate distally into cutting element (244) of tissue cutting washer (240). Optionally, in response to such penetration, tissue cutting washer body (242) may fracture along knife cutting edge (200), thereby providing an audible indication (e.g., via a "snapping" sound) to the surgeon that the firing stroke is complete and that the clamped tissue has been fully stapled and severed.

As described above, and as shown in FIG. 12D, staple driver member (186) and knife member (194) may translate distally together through staple cartridge housing (162) as firing trigger (38) is actuated through a primary range of motion that results in stapling of the tissue. As shown in FIG. 12D, knife member (194) may then continue translating distally relative to a stationary staple driver member (186) as firing trigger (38) is further actuated through a final range of motion that results in cutting of the stapled tissue with knife (198). In this manner, the tissue clamped by end effector (16) is fully stapled before being severed.

As shown best in FIG. 7, a first lateral side of lower body portion (184) of cartridge housing (162) includes a detent arm (185) having a plurality of axially spaced recesses. Additionally, a first lateral side of base portion (188) of staple driver member (186) includes a laterally extending detent post (189), which is configured to detent axially along detent arm (206) as staple driver member (186) is driven distally through cartridge housing (162) when stapling clamped tissue. As shown best in FIG. 8, a second lateral side of base portion (188) of staple driver member (186) includes a detent arm (191) having a plurality of axially spaced recesses. Additionally, a second lateral side of base portion (196) of knife member (194) includes a laterally extending detent post (197), which is configured to detent axially along detent arm (191) as knife member (194) is driven distally through staple driver member (186) when cutting clamped tissue. Such detent features may provide the surgeon with tactile feedback when staple driver member (186) has been fully extended to staple the tissue, and subsequently when knife member (194) has been fully extended to cut the stapled tissue.

Once surgical stapler (10) has been fully fired, the surgeon releases firing trigger (38), which enables knife bar (70) and knife member (194) to automatically retract proximally relative to closure bar (50) via the resilient bias of knife return spring (130), described above. In the present version, knife bar (70) is operatively coupled with staple bar (60) such that proximal retraction of knife bar (70) relative to closure bar (50) also drives proximal retraction of staple bar (60) relative to closure bar (50); for example, via engagement of a lower tab (78) formed on a distal portion of knife bar (70) with a lower slot (66) formed in the underside of a distal portion of staple bar (60). Meanwhile, stapling detent features (185, 189) described above operate to maintain staple driver member (186) in its fully extended position within cartridge housing (162), such that distal lockout lever (270) disengages staple driver member (186). This allows distal lockout lever (270) to return to a raised lockout position and block re-actuation of firing trigger (38) now that staple cartridge unit (160) is spent. In this manner, distal lockout lever (270) prevents a surgeon from inadvertently re-firing spent staple cartridge unit (160) into tissue in a manner that would sever the tissue with knife (198) without applying staples.

Following release of firing trigger (38), the surgeon then depresses release button (110) on handle assembly (12) to permit closure trigger (36) and closure bar (50) to return to their unactuated states via the resilient bias of closure return spring (98), described above. Such proximal retraction of closure bar (50) draws cartridge housing (162) proximally away from anvil (210) so that the stapled and cut tissue may be released from end effector (16). Proximal retraction of closure bar (50) also draws staple bar (60) and knife bar (70) further proximally to their proximal home positions so that spent staple cartridge unit (160) may be removed from distal support structure (48) and replaced with a new staple cartridge unit (160).

E. Proximal Firing Lockout Mechanism of Surgical Stapler

In some instances, while actuating closure trigger (36) to clamp tissue within end effector (16) during a surgical procedure, an operator may inadvertently rest a finger on firing trigger (38), or firing trigger (38) may otherwise be pushed against a portion of the patient's body. Premature actuation of firing system (24), for example when end effector (16) is only partially closed on tissue, could result in malformation of staples (170) in the tissue and risk inadequate hemostasis when the tissue is then cut by knife (198). As described briefly above, firing lockout lever (140) of handle assembly (12) is operable to inhibit pivoting of firing trigger (38), and resultant actuation of staple driver member (186) and knife member (194), until end effector (16) is fully closed to adequately clamp the tissue before applying staples (170) and a cut line.

Figure 13:
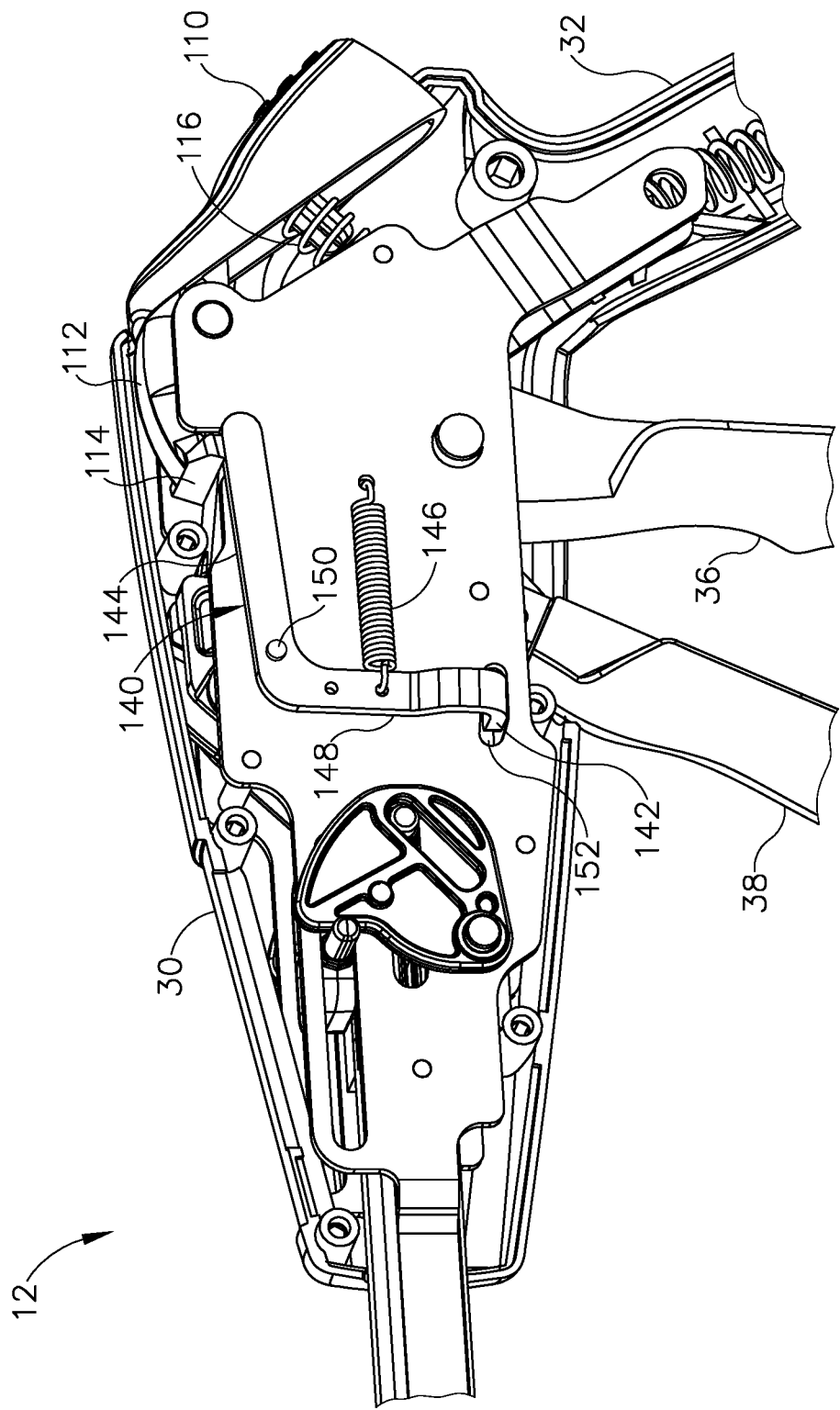
FIG. 13 depicts a perspective view of the handle assembly of the surgical stapler of FIG. 1A, with a portion of a housing thereof omitted for clarity, showing details of a pivotable firing lockout mechanism housed within the handle assembly.

As shown in FIG. 13, and as briefly described above, firing lockout lever (140) is pivotably mounted via a pivot pin (150) to an outer side of the proximal frame portion (42) of the left side plate (40). Firing lockout lever (140) of the present version has an L-like shape defining upper arm (144) and a lower leg (148) that depends downwardly from a distal end of upper arm (144), both extending in a plane parallel to proximal frame portion (42). Lower tab (142) extends perpendicularly from a lower end of lower leg (148) and projects laterally inward toward firing trigger (38) through a slot (152) formed in proximal frame portion (42) of side plate (40). Pivot pin (150) is positioned at the distal end of upper arm (144) and enables firing lockout lever (140) to pivot relative to side plate (40) between a lockout state shown in FIGS. 14A and 15A, and a bypass state shown in FIGS. 14B and 15B. Spring (146), shown in the form of an extension spring, is anchored at a proximal end to proximal frame portion (42) and at a distal end to lower leg (148). As described below, spring (146) is operable to resiliently bias firing lockout lever (140) toward the lockout state.

Figure 14A:
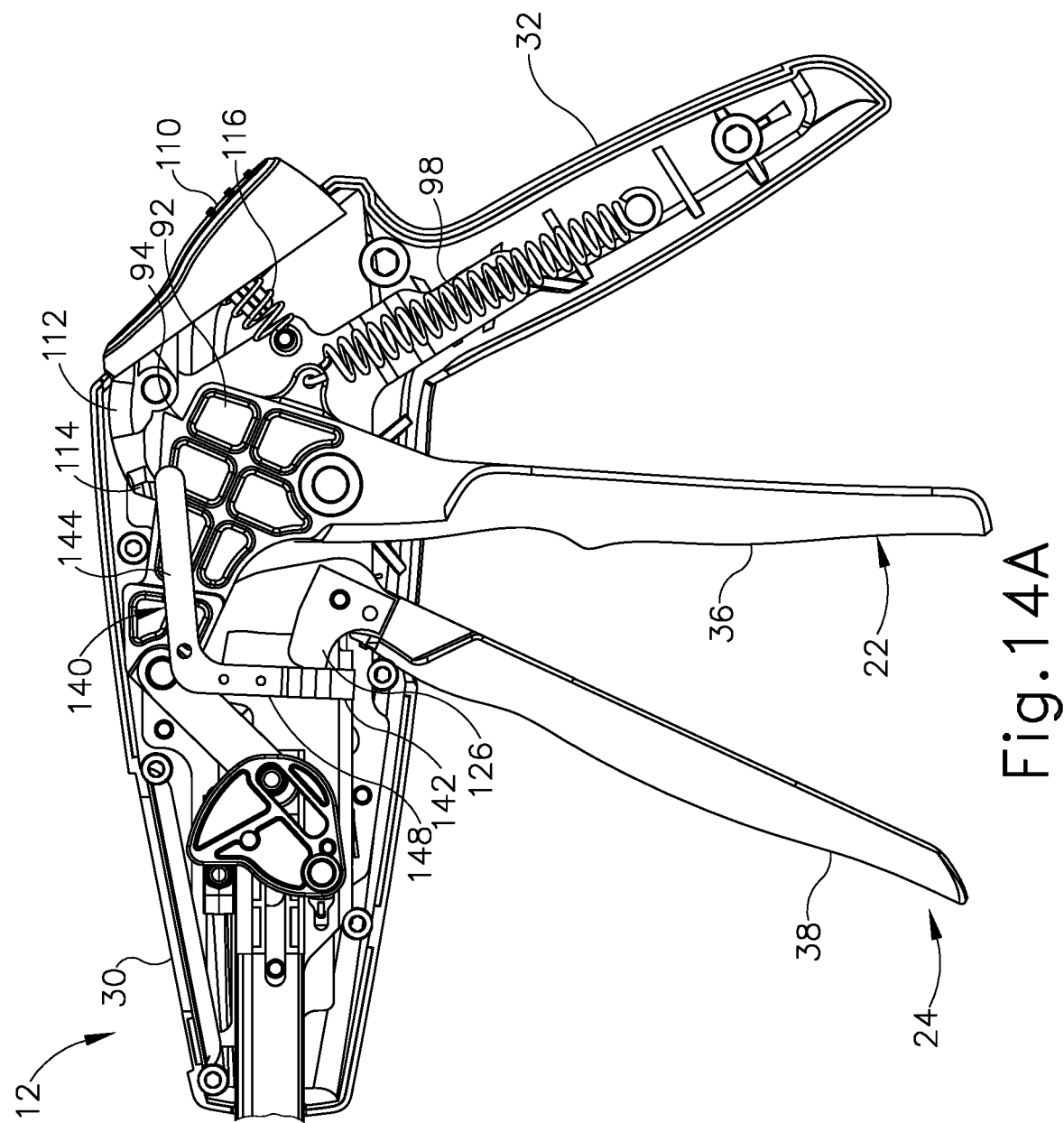
FIG. 14A depicts a side elevational view of the handle assembly of the surgical stapler of FIG. 1A, with certain components thereof omitted for clarity, showing the firing lockout mechanism in a lockout state while the closure system is in an unactuated state.
Figure 15A:
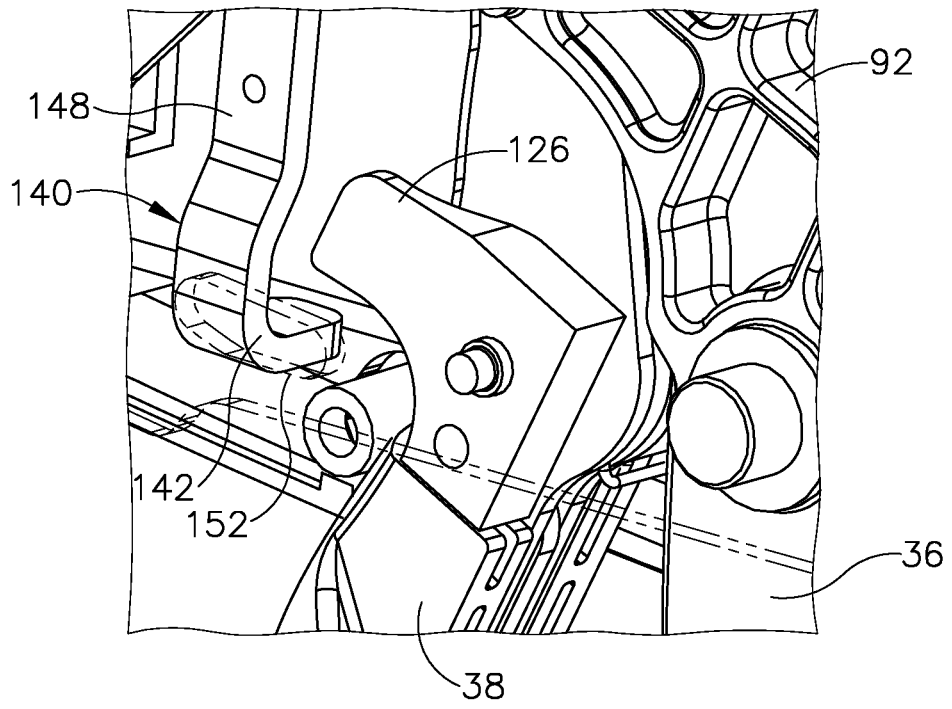
FIG. 15A depicts an enlarged perspective view of a portion of the firing trigger and the firing lockout mechanism of the surgical stapler of FIG. 1A, showing the firing lockout mechanism in the lockout state to inhibit actuation of the firing trigger.

As shown in FIGS. 14A and 15A, firing lockout lever (140) assumes the lockout state while closure system (22) is in any state other than a fully actuated to fully close end effector (16). In the lockout state, lower tab (142) of firing lockout lever (140) extends laterally beneath firing lockout projection (126) of firing trigger (38) and thus blocks firing trigger (38) from pivoting to actuate staple bar (60) and knife bar (70), described above. Firing lockout lever (140) is configured to maintain this lockout state throughout partial closure of end effector (16) via closure system (22), up until full closure of end effector (16).

Figure 14B:
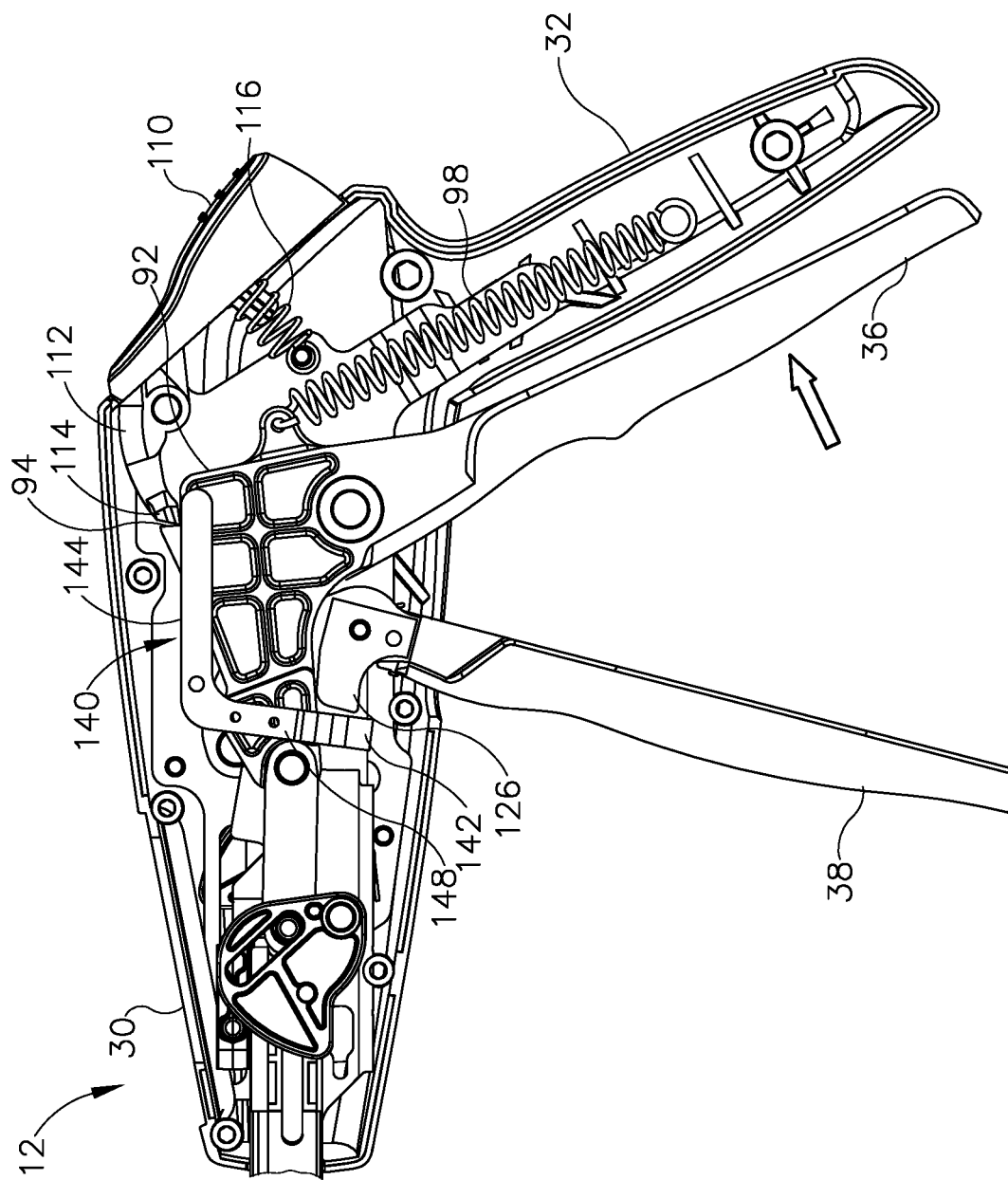
FIG. 14B depicts a side elevational view of the handle assembly of the surgical stapler of FIG. 1A, with certain components thereof omitted for clarity, showing the firing lockout mechanism moved to a bypass state in response to actuation of the closure system via the closure trigger to fully close the end effector.
Figure 14C:
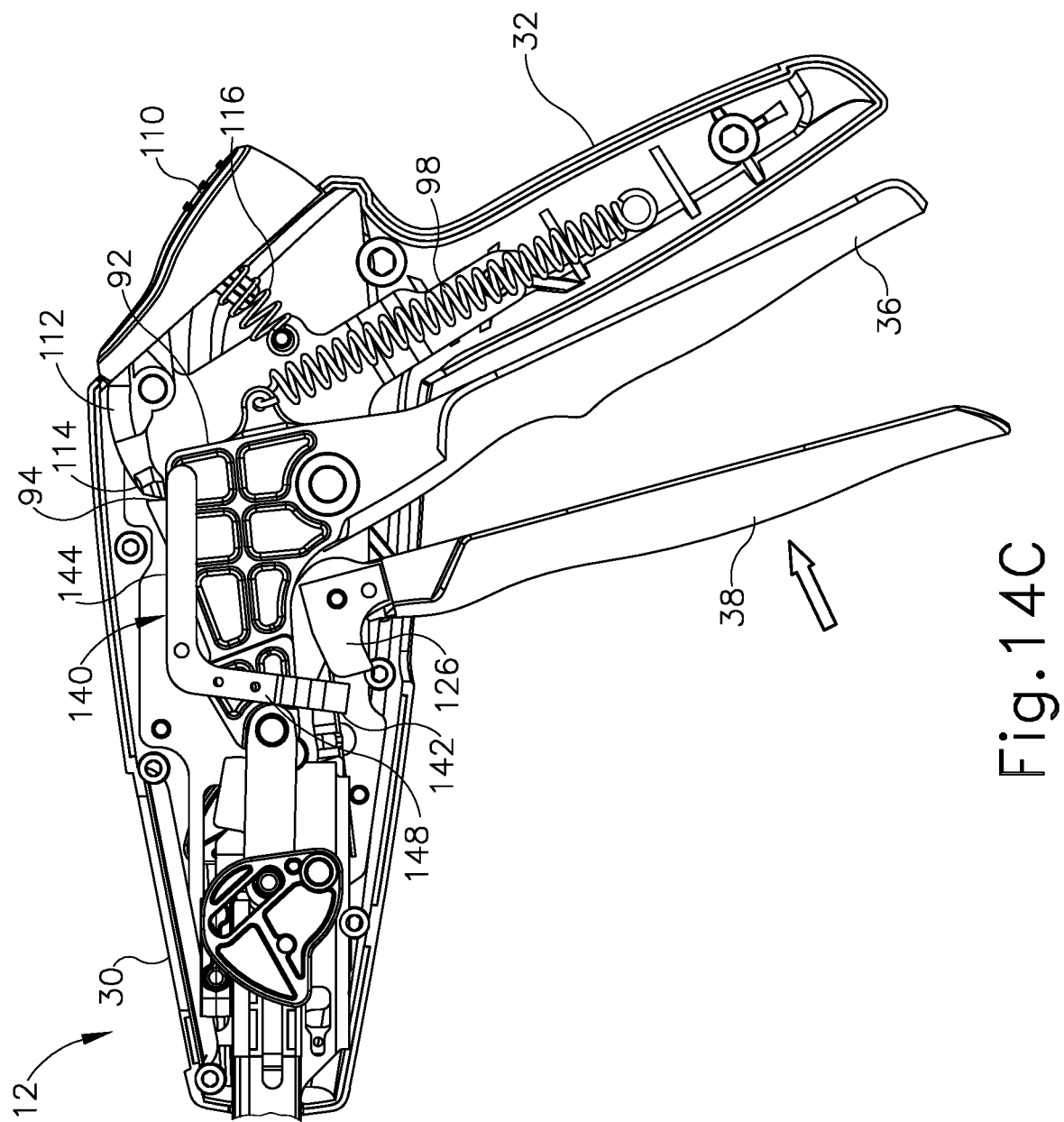
FIG. 14C depicts a side elevational view of the handle assembly of the surgical stapler of FIG. 1A, with certain components thereof omitted for clarity, showing actuation of the firing system via the firing trigger while the closure system remains in the fully actuated state and while the firing lockout mechanism is in the bypass state.
Figure 15B:
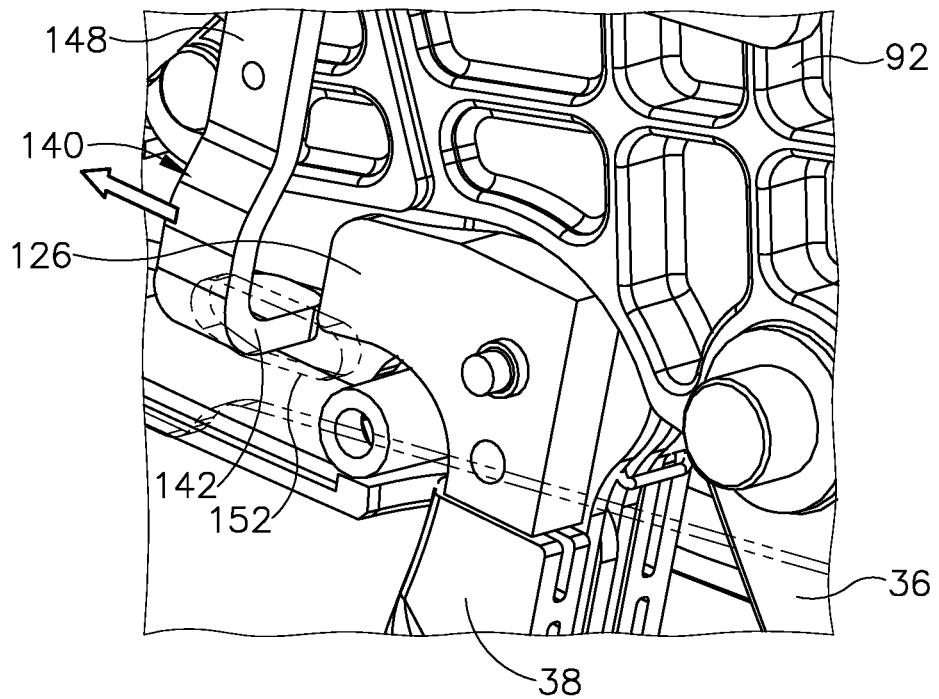
FIG. 15B depicts an enlarged perspective view of a portion of the firing trigger and the firing lockout mechanism of the surgical stapler of FIG. 1A, showing the firing lockout mechanism moved to the bypass state to permit actuation of the firing trigger.

As shown in FIG. 14B, and as briefly described above, as closure trigger (36) is squeezed toward pistol grip (32) to actuate closure bar (50) distally and thereby close end effector (16), pawl lug (114) of release button (110) slides across the upper edge of closure trigger upper arm (92). Upon reaching a fully actuated state to thereby place end effector (16) in a fully closed state, closure trigger (36) is rotationally oriented such that pawl lug (114) drops into proximal notch (94) formed in closure trigger upper arm (92), via the resilient bias imparted by release button spring (116). Upon dropping into notch (94), pawl lug (114) directly contacts an upper edge of a proximal end of lockout lever upper arm (144), and drives upper arm (144) downwardly. This engagement forces lockout lever (140) to pivot clockwise about pivot pin (150) such that lower tab (142) advances distally within slot (152) and out from beneath the underside of firing trigger projection (126), as seen in FIG. 15B. As shown in FIG. 14C, firing trigger (38) may then be actuated toward pistol grip (32) to actuate staple bar (60) and knife bar (70) distally to fire end effector (16).

As described above, after end effector (16) is fired into tissue, firing trigger (38) resiliently returns to an unactuated state upon being released by the operator. The operator may then depress release button (110) to raise pawl lug (114) from proximal notch (94) of closure trigger (36), thereby enabling closure trigger (36) to resiliently return to an unactuated state. Upon being raised from proximal notch (94), pawl lug (114) disengages upper arm (144) of firing lockout lever (140), thus enabling lockout lever (140) to return to the lockout state via the resilient bias of spring (146). Accordingly, lockout lever (140) prevents re-actuation of firing trigger (38) until closure trigger (36) has once again been fully actuated to fully close end effector (16). However, even when end effector (16) is again fully closed so as to provide proximal firing lockout lever (140) in a bypass state, re-firing of a used staple cartridge unit (160) may be prevented by distal lockout lever (140) (see FIGS. 9A-9B). As noted above, distal lockout lever (140) may be configured and operable in accordance with any of the teachings of U.S. patent application Ser. No. 16/395,359, entitled "Cartridge Based Lockout Mechanism for Right Angle Surgical Stapler," filed on Apr. 26, 2019, published as U.S. Pub. No. 2020/0337700 on Oct. 29, 2020, incorporated by reference above.

Figure 16:
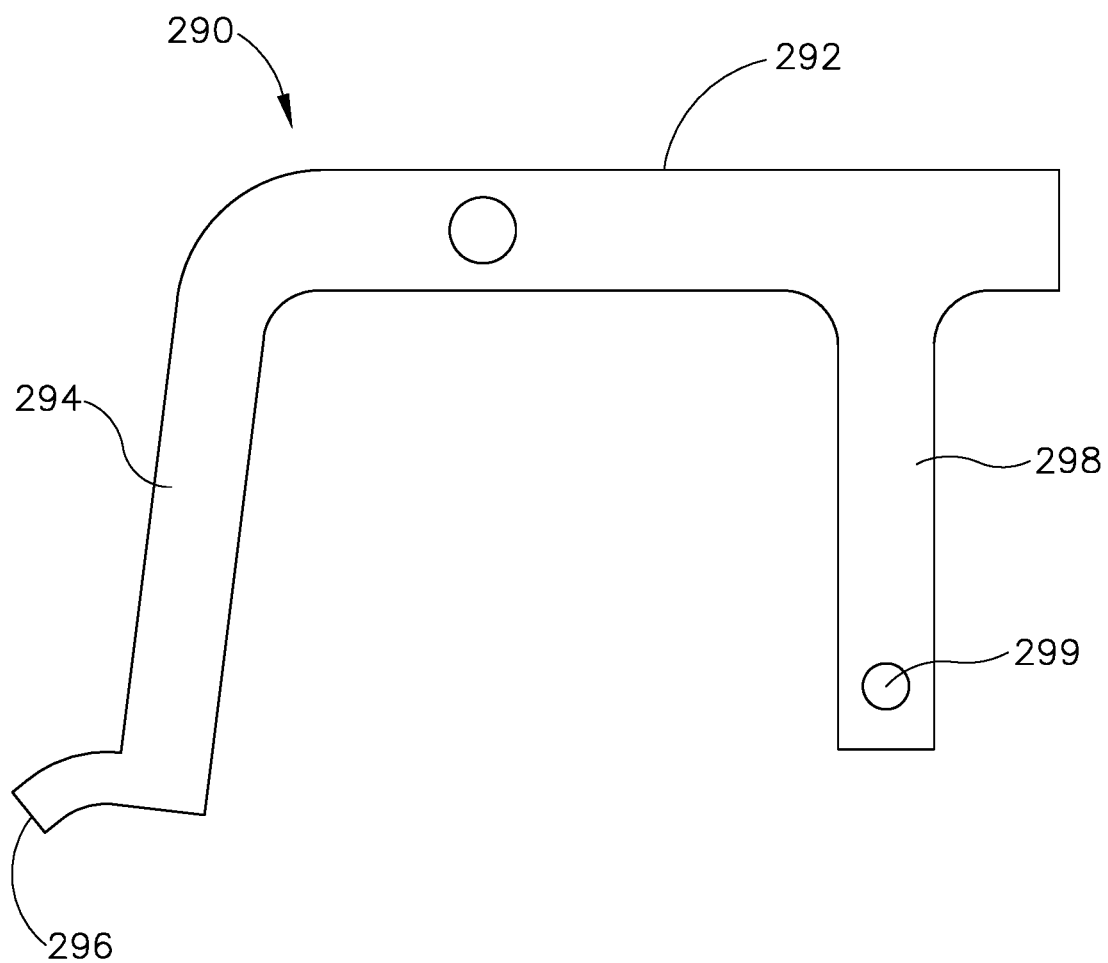
FIG. 16 depicts an exemplary alternative pivotable firing lockout mechanism suitable for use with the surgical stapler of FIG. 1A.

FIG. 16 shows an exemplary alternative firing lockout lever (290) suitable for use with surgical stapler (10) in place of firing lockout lever (140) described above, and which is similar to firing lockout lever (140) except as otherwise described below. Firing lockout lever (290) includes an upper arm (292), a distal leg (294) that depends downwardly from a distal end of upper arm (292) to define an L-like shape, and a lower tab (296) that extends laterally inwardly from a lower end of distal leg (294). Firing lockout lever (290) further includes a proximal leg (298) that depends downwardly form a proximal end of upper arm (292). A lower end of proximal leg (298) is configured to couple with a return spring (not shown) that resiliently biases firing lockout lever (290) toward a lockout position, similar to spring (146) described above. Accordingly, return spring is coupled to proximal leg (298) rather than distal leg (294), which provides a configuration that may be advantageous in some instances.

Lockout lever (290) is otherwise functionally similar to lockout lever (140). Specifically, lockout lever (290) is configured to pivot about a pivot point (299) between a lockout position in which lower tab (296) underlies projection (126) of firing trigger (38) and thus inhibits actuation of firing trigger (38); and a bypass position in which lower tab (296) is moved away from firing trigger projection (126) and thus permits actuation of firing trigger (38). Such actuation of lockout lever (290) is driven by pawl lug (114) of release button (110) in response to full actuation of closure trigger (36) for fully clamping end effector (16) on tissue.

II. Exemplary Alternative Firing Lockout Mechanisms

In some instances, it may be desirable to provide surgical stapler (10) with a firing lockout mechanism that differs in structure from firing lockout mechanism (140) described above, but which performs a similar function. The exemplary alternative firing lockout mechanisms (360, 440) described below are functionally similar to firing lockout mechanism (140). In that regard, each lockout mechanism (360, 440) is operable to inhibit actuation of a firing system unless the end effector is fully closed, thus protecting against malformation of staples in the patient tissue and resulting inadequate hemostasis. Like lockout mechanism (140) described above, each lockout mechanism (360, 440) described below is resiliently biased toward a lockout state that inhibits actuation of a firing trigger; and is configured to transition to a bypass state that permits actuation of the firing system in response to full actuation of the closure trigger to fully close the end effector.

A. Firing Lockout Mechanism Having Translatable Members

Figure 17:
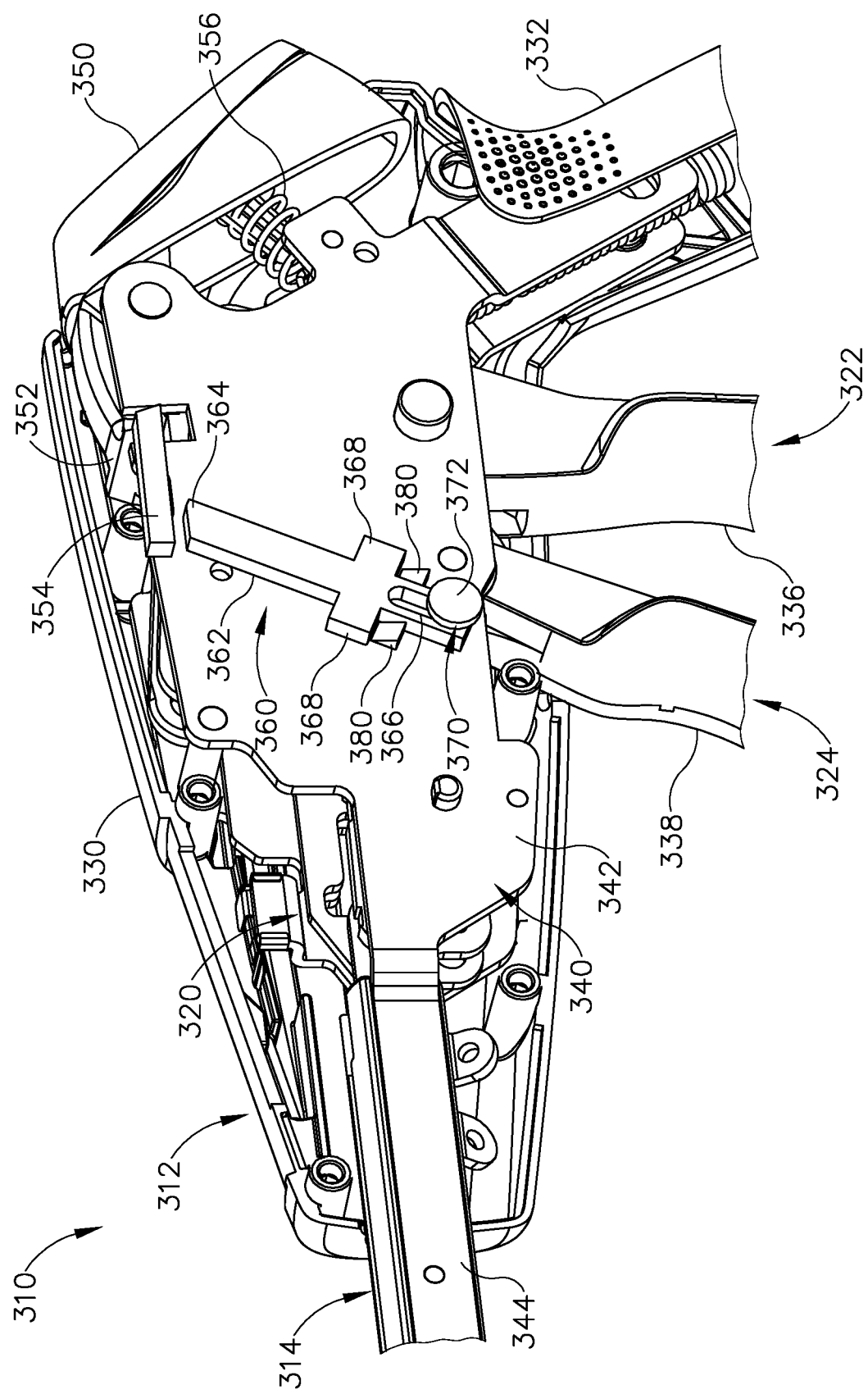
FIG. 17 depicts a perspective view of a handle assembly of another exemplary surgical stapler, with a portion of a housing thereof omitted for clarity, showing details of a translatable firing lockout mechanism housed within the handle assembly.

FIG. 17 shows a proximal portion of another exemplary right angle linear surgical stapler (310) that is similar to right angle linear surgical stapler (10) described above except as otherwise described below. Like surgical stapler (10), surgical stapler (310) includes a handle assembly (312), a shaft assembly (314) extending distally from handle assembly (312), and an end effector (not shown) similar to end effector (16) at a distal end of shaft assembly (314). Handle assembly (312) includes a handle housing (330), a pistol grip (332), a closure trigger (336), a firing trigger (338), and a proximal release button (350). A pair of longitudinally extending a cooperate to define a frame structure of stapler (310) that supports a tissue retaining pin actuation system (320), a closure system (322), and a firing system (324). Each side plate (340) includes a proximal frame portion (342), a medial shaft portion (344), and a distal jaw portion (not shown) similar to distal jaw portion (46).

Surgical stapler (310) includes a proximal firing lockout mechanism (360) that includes a translatable lockout plate (362) and a translatable lockout pin (370) movably mounted to proximal frame portion (342) of the left side plate (340); and a pair of ramps (380) extending outwardly from proximal frame portion (342). Lockout plate (362) has an elongate body with a free upper end (364), an elongate slot (366) formed at a lower end, and a pair of outwardly extending shoulders (368) disposed between upper end (364) and elongate slot (366). Lockout plate (362) extends in and translates along a plane parallel to proximal frame portion (342) of side plate (340). Lockout pin (370) extends transversely relative to lockout plate (362) and includes a pin head (372) and a pin shaft (374). Pin shaft (374) extends laterally through elongate slot (366) of lockout plate (362) and a corresponding opening (343) formed in proximal frame portion (342) of side plate (340) (see FIG. 19B), in a direction toward firing trigger (338). Pin head (372) is configured to slidably abut an outer surface of lockout plate (362) surrounding elongate slot (366). In the present version, a pair of ramps (380) project laterally outwardly from proximal frame portion (342) of side plate (340) and are positioned on either side of the lower portion of lockout plate (362) in which elongate slot (366) is disposed. In other versions, ramps (380) may be integrated into the structure of lockout plate (362), for example on either side of elongate slot (366).

As described below in connection with FIGS. 18A-19B, translatable lockout plate (362) and translatable lockout pin (370) are configured to cooperate with ramps (380) to transition lockout mechanism (360) between a lockout state in which pin (370) blocks actuation of firing trigger (338); and a bypass state in which pin (370) permits actuation of firing trigger (338). In transitioning between the lockout and bypass states, lockout plate (362) is configured to translate along a first axis that extends parallel to side plate (340), and lockout pin (370) is configured to translate along a lateral axis that extends transversely to the first axis. Similar to firing lockout levers (140, 290) described above, lockout plate (362) and lockout pin (370) are resiliently biased toward the lockout state by one or more resilient members (not shown).

Figure 18A:
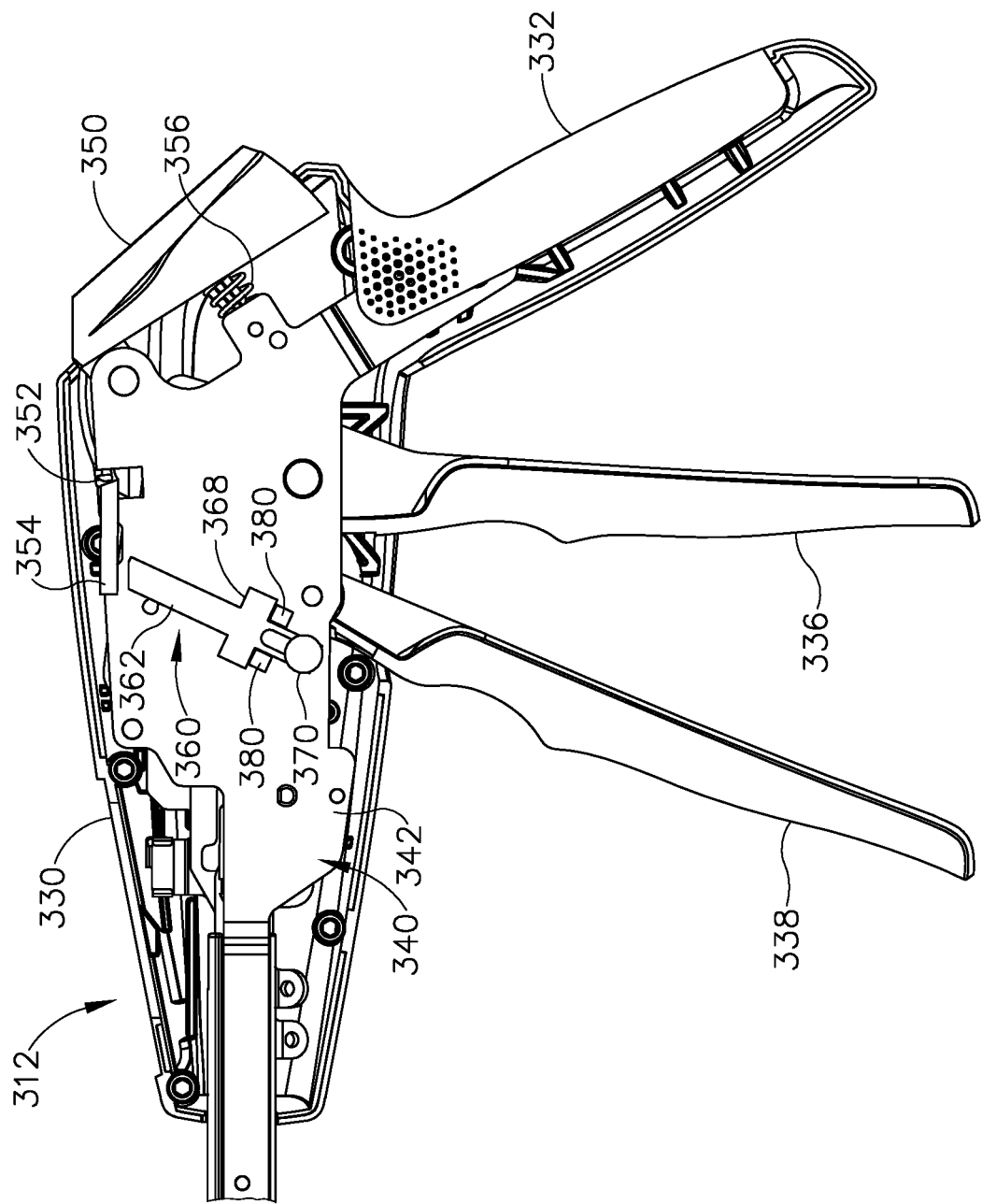
FIG. 18A depicts a side elevational view of the handle assembly of the surgical stapler of FIG. 17, with a portion of the housing omitted for clarity, showing the firing lockout mechanism in a lockout state while the closure system is in an unactuated state.
Figure 19A:
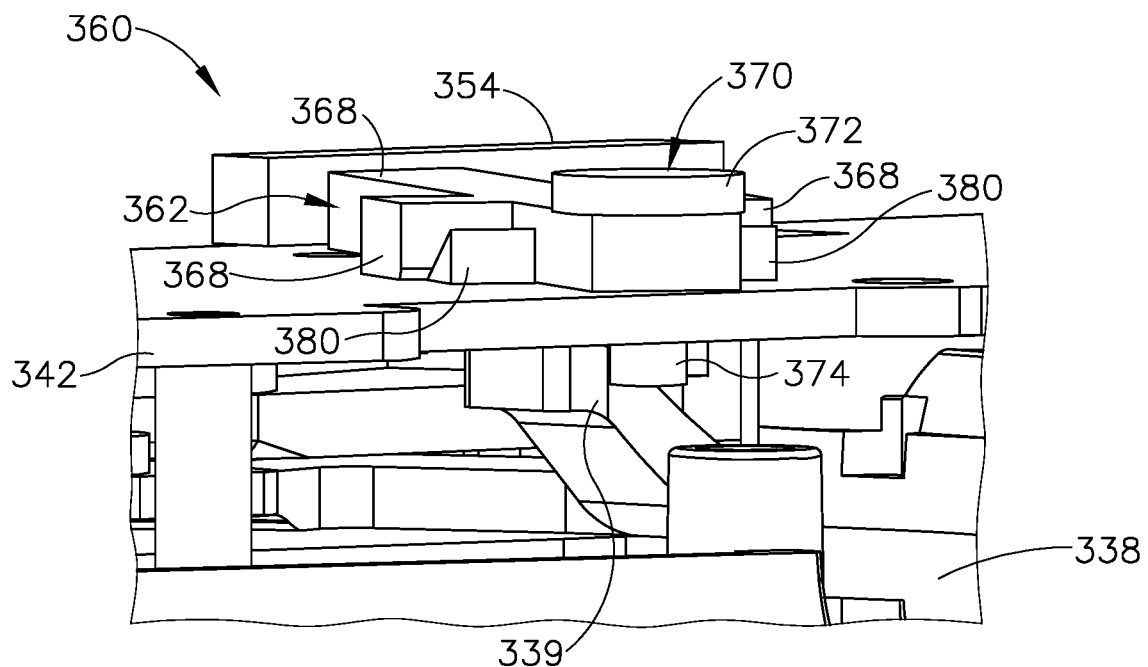
FIG. 19A depicts an enlarged perspective view of an underside of the handle assembly of the surgical stapler of FIG. 17, showing the firing lockout mechanism in the lockout state in which a translatable pin thereof is positioned to inhibit actuation of the firing trigger.

FIGS. 18A and 19A show firing lockout mechanism (360) in the lockout state, which lockout mechanism (360) is configured to maintain when closure trigger (336) is in any state other than fully actuated. In that regard, firing lockout mechanism (360) is configured to maintain the lockout state throughout partial actuation of closure trigger (336) and resulting partial closure of the end effector, up until full closure of the end effector. In the lockout state, lockout plate (362) is in a raised position such that lockout pin (370) is disposed at a lower end of elongate slot (366). As shown in FIG. 19A, pin (370) thus assumes a laterally inward position in which pin shaft (374) is positioned beneath an underside of a distal projection (339) of firing trigger (338), thus blocking firing trigger (338) from being actuated to fire the end effector.

Figure 18B:
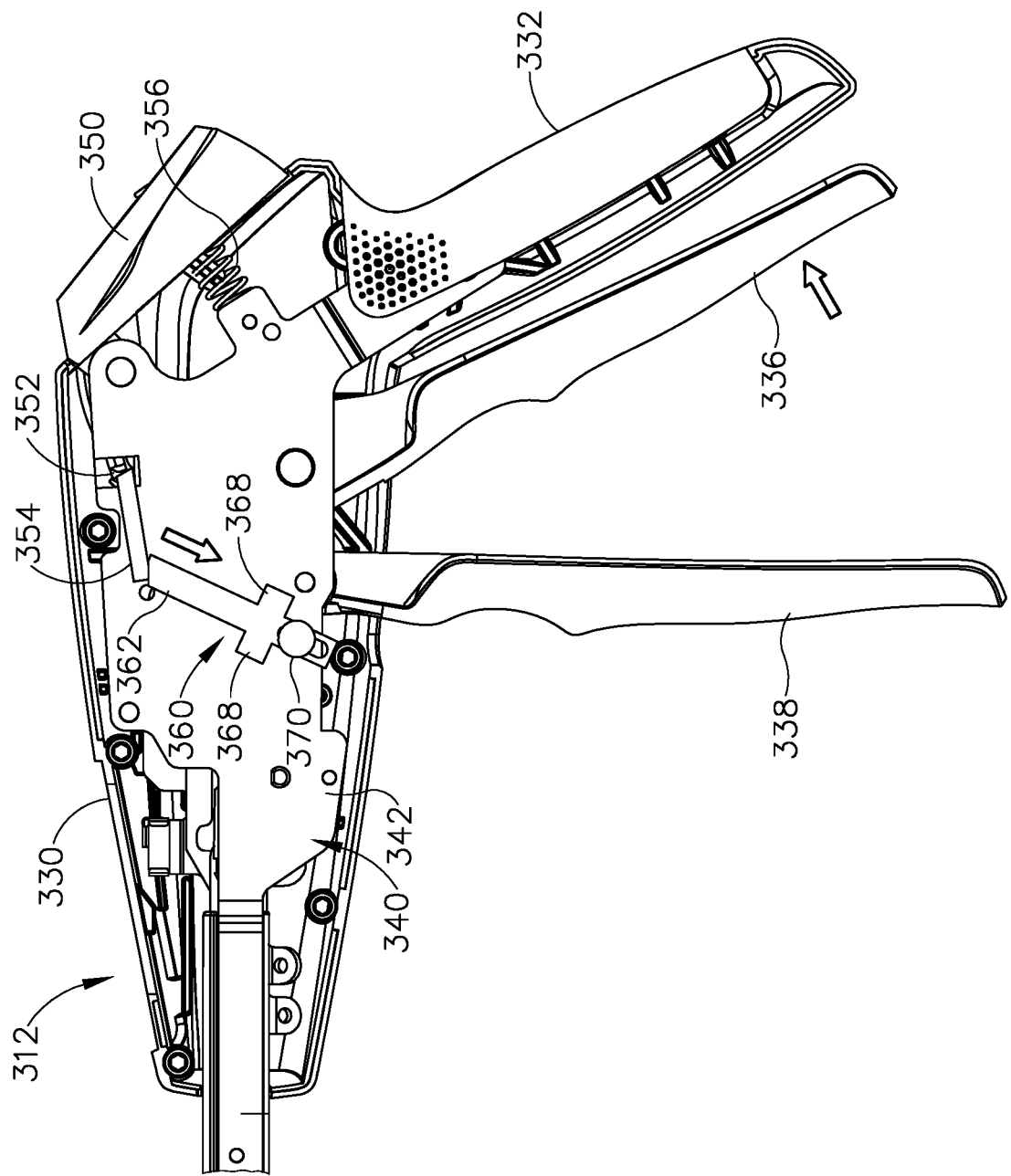
FIG. 18B depicts a side elevational view of the handle assembly of the surgical stapler of FIG. 17, with a portion of the housing omitted for clarity, showing the firing lockout mechanism moved to a bypass state in response to actuation of the closure system via the closure trigger to fully close the end effector.
Figure 19B:
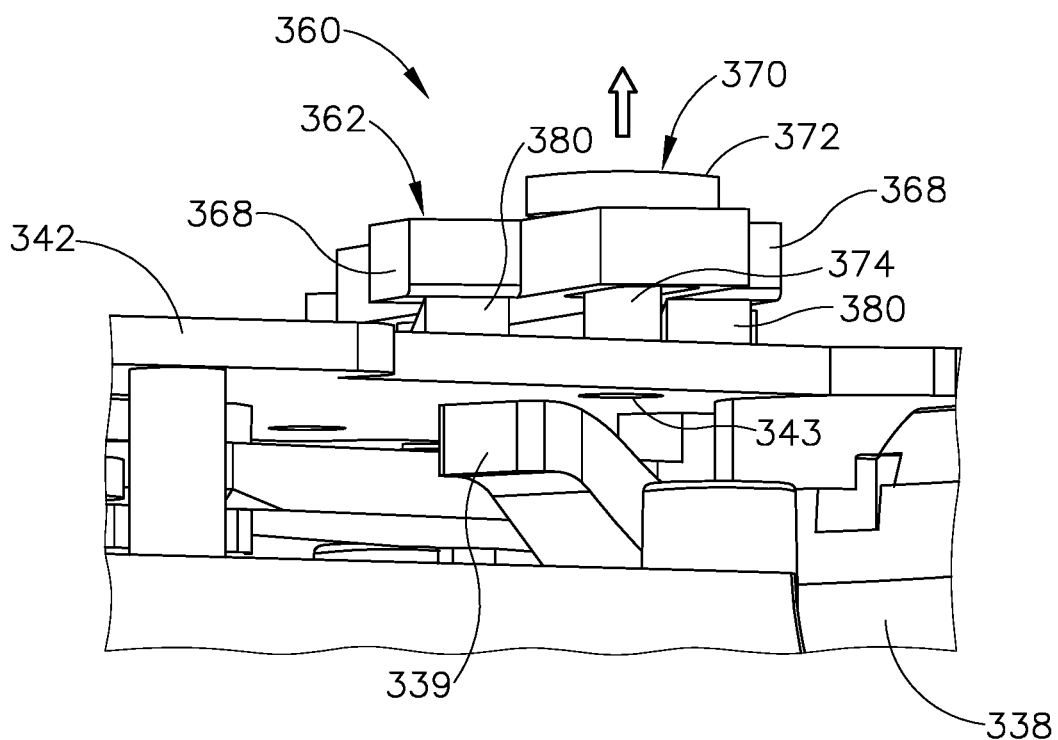
FIG. 19B depicts an enlarged perspective view of an underside of the handle assembly of the surgical stapler of FIG. 17, showing the firing lockout mechanism in the bypass state in which the translatable pin is positioned to permit actuation of the firing trigger.

As shown in FIG. 18B, full actuation of closure trigger (336) for fully closing the end effector rotationally aligns an upper notch (not shown) of closure trigger (336), similar to notch (94) of closure trigger (36), with a pawl lug (352) of release button (350). Via resilient bias provided by a release button spring (356), pawl lug (352) drops into the upper notch of closure trigger (336) to lock closure trigger (336) in the fully actuated position. This downward motion of pawl lug (352) causes a distal lug extension (354) to engage upper end (364) of lockout plate (362), thus forcing lockout plate (362) to translate downwardly and distally along side plate (340) to a lowered plate position. Because lockout pin (370) is fixed along the translation axis of lockout plate (362), pin (370) advances to the upper proximal end of elongate slot (366). Simultaneously, as best in FIG. 19B, plate shoulders (368) advance downwardly and distally along ramps (380), which drive lockout plate (362) laterally away from side plate (340). In turn, lockout plate (362) draws lockout pin (370) laterally away from firing trigger (338), via pin head (372), thus providing lockout mechanism (360) in the bypass state. As shown in FIG. 19B, pin shaft (374) is withdrawn from the underside of firing trigger projection (339) such that firing trigger (338) is free to actuate toward pistol grip (332) for firing the end effector.

Upon actuation of release button (350) by an operator, pawl lug (352) disengages the upper notch of closure trigger (336), thus allowing closure trigger (336) to pivotably return to an unactuated state for releasing tissue from the end effector. Simultaneously, lug extension (354) releases its downwardly directed force on upper end (364) of lockout plate (362). Via resilient bias, lockout plate (362) translates upwardly to return to the raised plate position such that plate shoulders (368) disengage ramps, thus allowing lockout plate (362) to draw laterally toward side plate (340) as lockout plate (362) reassumes the raised position. As a result, and via resilient bias, lockout pin (370) translates laterally inwardly through slot (366) and opening (343) to reengage firing trigger projection (339) and thus return lockout mechanism (360) to the lockout state.

B. Firing Lockout Mechanism Configured to Engage Firing Bar

Figure 20A:
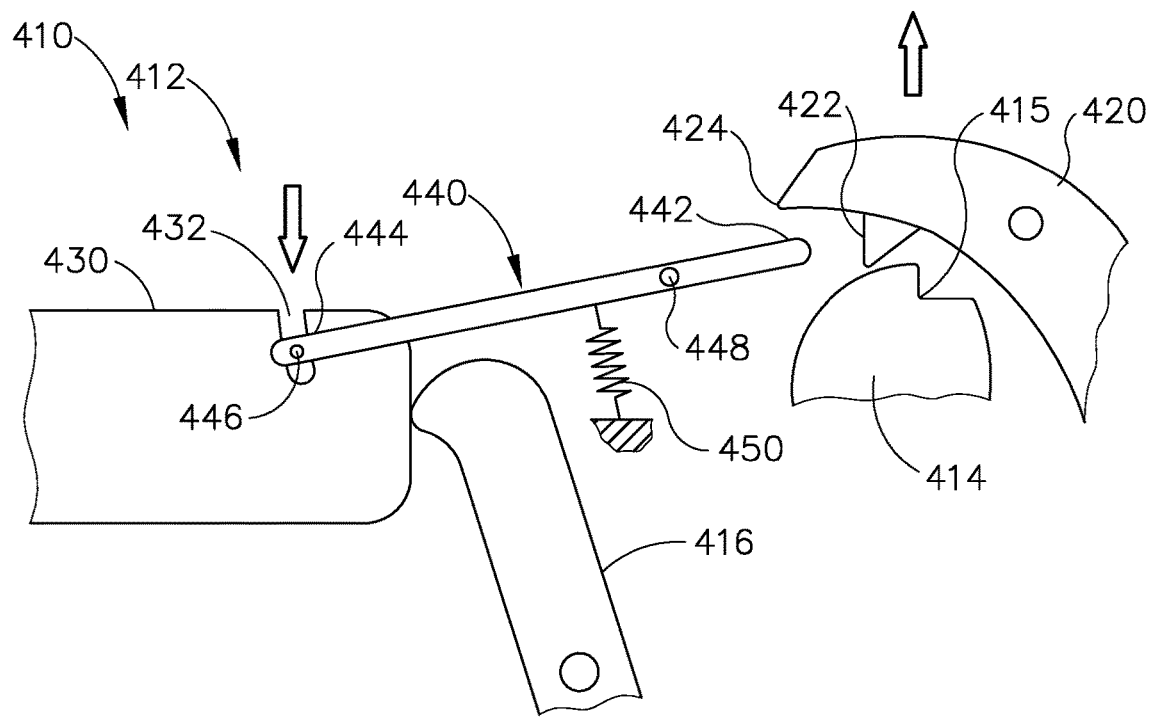
FIG. 20A depicts a schematic side view of portions of select movable components housed within a handle assembly of another exemplary surgical stapler, showing a pivotable firing lockout mechanism in a lockout state while a closure system is in an unactuated state.
Figure 20B:
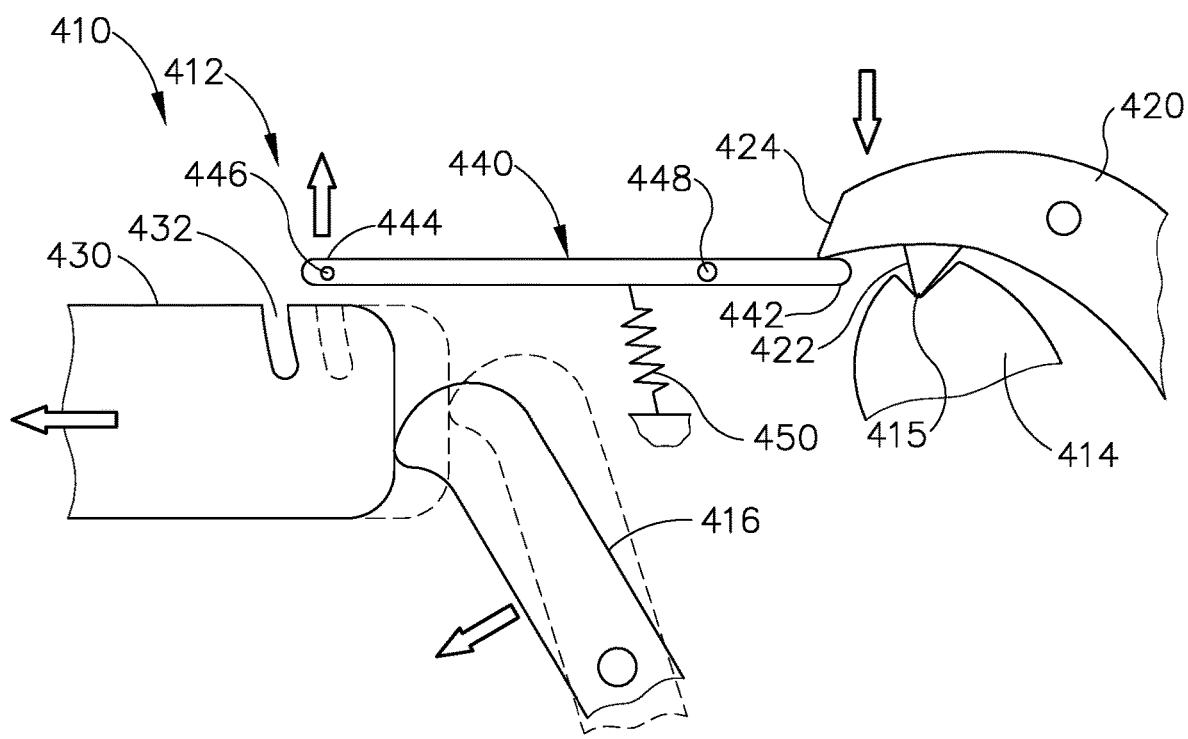
FIG. 20B depicts a schematic side view of portions of the select movable components housed with the handle assembly of the surgical stapler of FIG. 20A, showing the firing lockout mechanism moved to a bypass state in response to actuation of the closure system to fully close an end effector, and showing actuation of a firing system.

FIGS. 20A-20B show portions of select components of a handle assembly (412) of another exemplary surgical stapler (410), which may be a right angle linear surgical stapler similar to staplers (10, 310) described above. Handle assembly (412) includes a pivotable closure trigger (414), a pivotable firing trigger (416) arranged distally of closure trigger (414), and a release button (420). An elongate firing bar (430) extends distally from handle assembly (412) and is configured to be actuated distally by firing trigger (416) to fire an end effector (not shown) of stapler (410), which may be similar to end effector (16) described above. A proximal end of firing bar (430) includes a vertical slot (432) configured to be engaged by a firing lockout mechanism (430) described below. Firing bar (430) may comprise a staple bar similar to staple bar (60), a knife bar similar to knife bar (70), or both.

Firing lockout mechanism (430) of surgical stapler (410) is shown in the form of a pivotable lockout lever. Lockout lever (440) extends longitudinally between a proximal end (442) and a distal end (444) having a lateral projection (446), and is configured to pivot about a lateral axis defined by a pivot pin (448). As shown in FIGS. 20A-20B, lockout lever (440) is configured to pivot between a lockout state in which lockout lever (440) inhibits actuation of firing bar (430), and a bypass state in which lockout lever (440) permits actuation of firing bar (430).

In the lockout state shown in FIG. 20A, distal lever end (444) is positioned downwardly such that lateral projection (446) is received within vertical slot (432) of firing bar (430). This engagement between lateral projection (446) and vertical slot (432) inhibits longitudinal actuation of firing bar (430) by firing trigger (416), and resulting firing of the end effector. It will be appreciated that such longitudinal locking of firing bar (430) by lockout lever (440) effectively inhibits actuation of firing trigger (416). Accordingly, in versions in which firing bar (430) comprises a staple bar and a knife bar, either of such bars may be engaged by lockout lever (440) to inhibit actuation of firing trigger (416) and resulting firing of the end effector. Lockout lever (440) is resiliently biased toward the lockout state by a resilient member shown in the form of an extension spring (450), which is coupled to a portion of lockout lever (440) distal to pivot pin (448). Accordingly, lockout lever (440) is configured to maintain the lockout state while closure trigger (414) is in an unactuated state or any partially actuate state, as shown in FIG. 20A.

As shown in FIG. 20B, full actuation of closure trigger (414) to fully close the end effector of surgical stapler (410) rotationally aligns a proximal upper notch (415) of closure trigger (414) with a locking pawl (422) of release button (420). Under resilient bias provided by a release button spring (not shown), locking pawl (422) drops downwardly into notch (415), thereby locking closure trigger (414) in the fully actuated state to maintain the end effector in the fully closed state. Simultaneously, a distal extension (424) of release button (420) engages and drives proximal lever end (442) downwardly, forcing lockout lever (440) to pivot about pivot pin (448) such that distal lever end (444) raises, thereby disengaging lateral projection (446) from vertical slot (432) of firing bar (430). Accordingly, firing bar (430) is now free to translate distally in response to actuation of firing trigger (416) for firing the end effector. After firing of the end effector, firing bar (430) retracts proximally to its home position shown in FIG. 20A, and release button (420) is depressed by the surgeon to disengage locking pawl (422) from closure trigger (414), thus allowing closure trigger (414) to return to an unactuated position. Simultaneously, distal extension (424) disengages proximal lever end (442), thus enabling lockout lever (440) to pivot counter-clockwise so that distal lever end (444) reengages firing bar (430) to re-establish the lockout state.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical stapler comprising: (a) a body; (b) a shaft assembly extending distally from the body; (c) an end effector at a distal end of the shaft assembly, wherein the end effector is actuatable between an open state for receiving tissue and a closed state for clamping the tissue; (d) a closure system operatively coupled with the end effector, wherein the closure system is operable to actuate the end effector from the open state to the closed state; (e) a firing system operatively coupled with the end effector, wherein the firing system is operable to actuate the end effector in the closed state to staple the clamped tissue; and (f) a firing lockout mechanism operatively coupled with the firing system, wherein the firing lockout mechanism is movable between a lockout state in which the firing lockout mechanism inhibits actuation of the firing system, and a bypass state in which the firing lockout mechanism permits actuation of the firing system, wherein the firing lockout mechanism is configured to maintain the lockout state until the end effector assumes the closed state, wherein the firing lockout mechanism is configured to transition from the lockout state to the bypass state in response to the end effector assuming the closed state.

EXAMPLE 2

The surgical stapler of Example 1, wherein the firing lockout mechanism is resiliently biased toward the lockout state.

EXAMPLE 3

The surgical stapler of any of the preceding Examples, wherein the firing lockout mechanism comprises a projection that extends transversely to a longitudinal axis of the shaft assembly, wherein the projection is configured to engage the firing system in the lockout state and thereby inhibit actuation of the firing system.

EXAMPLE 4

The surgical stapler of any of the preceding Examples, wherein the firing lockout mechanism is configured to remain stationary in the lockout state throughout partial actuation of the closure system for partially closing the end effector, wherein the firing lockout mechanism is configured to move to the bypass state in response to full actuation of the closure system for placing the end effector in the closed state.

EXAMPLE 5

The surgical stapler of any of the preceding Examples, further comprising a closure lock feature operatively coupled with the closure system, wherein the closure lock feature is operable to releasably lock the closure system in a fully actuated state to maintain the end effector in the closed state and simultaneously drive the firing lockout mechanism from the lockout state to the bypass state.

EXAMPLE 6

The surgical stapler of Example 5, wherein the closure lock feature is resiliently biased into engagement with the closure system and the firing lockout mechanism.

EXAMPLE 7

The surgical stapler of any of Examples 5 through 6, wherein the closure lock feature is positioned to contact an upper end of the firing lockout mechanism.

EXAMPLE 8

The surgical stapler of any of Examples 5 through 7, further comprising a closure release feature operatively coupled with the closure lock feature, wherein in response to a user input the closure release feature is operable to actuate the closure lock feature to disengage the closure system and thereby permit the end effector to return to the open state, and simultaneously permit the firing lockout mechanism to return to the lockout state.

EXAMPLE 9

The surgical stapler of any of the preceding Examples, wherein the firing lockout mechanism comprises a lever configured to pivot between the lockout state and the bypass state.

EXAMPLE 10

The surgical stapler of any of the preceding Examples, wherein the firing lockout mechanism comprises a translating member configured to translate between the lockout state and the bypass state.

EXAMPLE 11

The surgical stapler of any of the preceding Examples, wherein the firing lockout mechanism comprises: (i) a first moveable member, and (ii) a second movable member operatively coupled with the first movable member, wherein the second moveable member is configured to engage and thereby inhibit actuation of the firing system in the lockout state, wherein in response to the end effector assuming the closed state, the first moveable member is configured to drive the second movable member out of engagement with the firing system and thereby provide the firing lockout mechanism in the bypass state.

EXAMPLE 12

The surgical stapler of Example 11, herein the first moveable member is configured to translate along a first axis, wherein the second moveable member is configured to translate along a second axis that is perpendicular to the first axis.

EXAMPLE 13

The surgical stapler of any of Examples 11 through 12, wherein the firing lockout mechanism further comprises a ramp, wherein the ramp is configured to drive the second moveable member away from the firing system in response to movement of the first moveable member when the end effector assumes the closed state.

EXAMPLE 14

The surgical stapler of any of Examples 11 through 13, wherein the first moveable member comprises a plate, wherein the second moveable member comprises a pin.

EXAMPLE 15

The surgical stapler of any of the preceding Examples, wherein the closure system comprises a pivotable closure trigger operable to actuate the end effector between the open state and the closed state, wherein the firing system comprises a pivotable firing trigger operable to actuate the end effector to fire staples into tissue clamped by the end effector in the closed state, wherein the firing lockout mechanism is operable to inhibit actuation of the firing trigger in the lockout state and permit actuation of the firing trigger in the bypass state.

EXAMPLE 16

A surgical stapler comprising: (a) a body; (b) a shaft assembly extending distally from the body; (c) an end effector at a distal end of the shaft assembly, wherein the end effector is actuatable between an open state for receiving tissue and a closed state for clamping the tissue; (d) a closure system operatively coupled with the end effector, wherein the closure system is operable to actuate the end effector from the open state to the closed state; (e) a closure lock feature operatively coupled with the closure system, wherein the closure lock feature is operable to releasably lock the closure system in an actuated state to maintain the end effector in the closed state; (f) a firing system operatively coupled with the end effector, wherein the firing system is operable to actuate the end effector in the closed state to staple the clamped tissue; and (g) a firing lockout mechanism operatively coupled with the firing system and the closure lock feature, wherein the firing lockout mechanism is movable between a lockout state in which the firing lockout mechanism inhibits actuation of the firing system, and a bypass state in which the firing lockout mechanism permits actuation of the firing system, wherein the firing lockout mechanism is configured to driven from the lockout state to the bypass state by the closure lock feature as the closure lock feature locks the closure system in the actuated state.

EXAMPLE 17

The surgical stapler of Example 16, wherein the closure lock feature is housed within the body, wherein the closure lock feature is configured to drive the firing lockout mechanism into the bypass state while locking the closure system in the actuated state.

EXAMPLE 18

The surgical stapler of any of Examples 16 through 17, wherein the closure lock feature is disengageable from the closure system in response to a user input, wherein the firing lockout mechanism is configured to transition from the bypass state to the lockout state in response to disengagement of the closure lock feature from the closure system.

EXAMPLE 19

A surgical stapler comprising: (a) a body, wherein the body includes a body frame structure; (b) a shaft assembly extending distally from the body; (c) an end effector at a distal end of the shaft assembly, wherein the end effector is actuatable between an open state for receiving tissue and a closed state for clamping the tissue; (d) a closure system supported by the body frame structure and operatively coupled with the end effector, wherein the closure system is operable to actuate the end effector from the open state to the closed state; (e) a firing system supported by the body frame structure and operatively coupled with the end effector, wherein the firing system is operable to actuate the end effector in the closed state to staple the clamped tissue; and (f) a firing lockout mechanism movably coupled to the body frame structure, wherein the firing lockout mechanism is movable relative to the body frame structure between a first position in which the firing lockout mechanism inhibits actuation of the firing system, and a second position in which the firing lockout mechanism permits actuation of the firing system, wherein the firing lockout mechanism is resiliently biased toward the first position, wherein the firing lockout mechanism is configured to be driven into the second position and thereby permit actuation of the firing system in response to the end effector assuming the closed state.

EXAMPLE 20

The surgical stapler of Example 19, wherein the closure system comprises a pivotable closure trigger supported by the body frame structure, wherein the firing lockout mechanism is configured to remain stationary in the first position throughout partial actuation of the closure trigger for partially closing the end effector, wherein the firing lockout mechanism is configured to move to the second position in response to full actuation of the closure trigger for placing the end effector in the closed state.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. patent application Ser. No. 16/395,357, entitled "Tissue Cutting Washer for Right Angle Surgical Stapler," filed on Apr. 26, 2019, published as U.S. Pub. No. 2020/0337698 on Oct. 29, 2020; U.S. patent application Ser. No. 16/395,359, entitled "Cartridge Based Lockout Mechanism for Right Angle Surgical Stapler," filed on Apr. 26, 2019, published as U.S. Pub. No. 2020/0337700 on Oct. 29, 2020; and U.S. patent application Ser. No. 16/395,364, entitled "Staple Retainer for Right Angle Surgical Stapler," filed on Apr. 26, 2019, published as U.S. Pub. No. 2020/0337701 on Oct. 29, 2020, issued as U.S. Pat. No. 11,166,721 on Nov. 9, 2021, the disclosures of which are incorporated by reference above.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
(a) a body;
(b) a shaft assembly extending distally from the body;
(c) an end effector at a distal end of the shaft assembly, Wherein the end effector is actuatable between an open state for receiving tissue and a closed state for clamping the tissue;
(d) a closure system operatively coupled with the end effector, wherein the closure system is operable to actuate the end effector from the open state to the closed state;
(e) a firing system operatively coupled with the end effector, wherein the firing system includes a firing trigger pivotable about a pivot axis and configured to be directly contacted by a user to actuate the end effector in the closed state to staple the clamped tissue; and
(f) a firing lockout mechanism operatively coupled with the firing system, wherein the firing lockout mechanism is movable between a lockout state in which the firing lockout mechanism directly contacts a portion of the firing trigger at a location distal to the pivot axis and thereby inhibits actuation of the firing system and a bypass state in which the firing lockout mechanism permits actuation of the firing system,
wherein the firing lockout mechanism is configured to maintain the lockout state until the end effector assumes the closed state,
wherein the firing lockout mechanism is configured to transition from the lockout state to the bypass state in response to the end effector assuming the closed state.

2. The surgical stapler of claim 1, wherein the firing lockout mechanism is resiliently biased toward the lockout state.

3. The surgical stapler of claim 1, wherein the firing lockout mechanism comprises a projection that extends transversely to a longitudinal axis of the shaft assembly, wherein the projection is configured to engage the firing system in the lockout state and thereby inhibit actuation of the firing system.

4. The surgical stapler of claim 1, wherein the tiring lockout mechanism is configured to remain stationary in the lockout state throughout partial actuation of the closure system for partially closing the end effector, wherein the firing lockout mechanism is configured to move to the bypass state in response to full actuation of the closure system for placing the end effector in the closed state.

5. The surgical stapler of claim 1, further comprising a closure lock feature operatively coupled with the closure system, wherein the closure lock feature is operable to releasably lock the closure system in a fully actuated state to maintain the end effector in the closed state and simultaneously drive the firing lockout mechanism from the lockout state to the bypass state.

6. The surgical stapler of claim 5, wherein the closure lock feature is resiliently biased into engagement with the closure system and the firing lockout mechanism.

7. The surgical stapler of claim 5, Wherein the closure lock feature is positioned to contact an upper end of the firing lockout mechanism.

8. The surgical stapler of claim 5, further comprising a closure release feature operatively coupled with the closure lock feature, wherein in response to a user input the closure release feature is operable to actuate the closure lock feature to disengage the closure system and thereby permit the end effector to return to the open state, and simultaneously permit the firing lockout mechanism to return to the lockout state.

9. The surgical stapler of claim 1, wherein the firing lockout mechanism comprises a lever housed within the body and configured to pivot between the lockout state and the bypass state.

10. The surgical stapler of claim 1, wherein the firing lockout mechanism comprises a translating member housed within the body and configured to translate between the lockout state and the bypass state.

11. The surgical stapler of claim 1, wherein the firing lockout mechanism comprises:
(i) a first moveable member, and
(ii) a second movable member operatively coupled with the first movable member,
wherein the second moveable member is configured to engage and thereby inhibit actuation of the tiring system in the lockout state,
wherein in response to the end effector assuming the closed state, the first moveable member is configured to drive the second movable member out of engagement with the firing system and thereby provide the firing lockout mechanism in the bypass state.

12. The surgical stapler of claim 11, wherein the first moveable member is configured to translate along, a first axis, wherein the second moveable member is configured to translate along a second axis that is perpendicular to the first axis.

13. The surgical stapler of claim 11, wherein the firing lockout mechanism further comprises a ramp, wherein the ramp is configured to drive the second moveable member away from the firing system in response to movement of the first moveable member when the end effector assumes the closed state.

14. The surgical stapler of claim 11, wherein the first moveable member comprises a plate, wherein the second moveable member comprises a pin.

15. The surgical stapler of claim 1, wherein the firing trigger includes a portion that is external to the body, wherein the closure system comprises a pivotable closure trigger operable to actuate the end effector between the open state and the closed state, wherein the firing lockout mechanism is operable to inhibit actuation of the firing trigger in the lockout state and permit actuation of the firing trigger in the bypass state.

16. A surgical stapler comprising:
(a) a body;
(b) a shaft assembly extending distally from the body;
(c) an end effector at a distal end of the shaft assembly, wherein the end effector is actuatable between an open state for receiving tissue and a closed state for clamping the tissue;
(d) a closure system operatively coupled with the end effector, wherein the closure system is operable to actuate the end effector from the open state to the closed state;
(e) a closure lock feature operatively coupled with the closure system, wherein the closure lock feature is operable to releasably lock the closure system in an actuated state to maintain the end effector in the closed state;
(f) a firing system operatively coupled with the end effector, wherein the firing system is operable to actuate the end effector in the closed state to staple the clamped tissue; and a rigid firing lockout mechanism operatively coupled with the firing system and the closure lock feature, wherein the tiring lockout mechanism is movable between a lockout state in which the firing lockout mechanism inhibits actuation of the firing system, and a bypass state in which the firing lockout mechanism permits actuation of the firing system,
wherein the closure lock feature is configured to exert a compressive force on and thereby drive the firing lockout mechanism relative to the body from the lockout state to the bypass state as the closure lock feature locks the closure system in the actuated state.

17. The surgical stapler of claim 16, wherein the closure lock feature is disengageable from the closure system in response to a user input, wherein the firing lockout mechanism is configured to transition from the bypass state to the lockout state in response to disengagement of the closure lock feature from the closure system.

18. The surgical stapler of claim 16, wherein the closure lock feature is configured to maintain the firing lockout mechanism in the bypass state while the closure system is in the actuated state, wherein the surgical stapler further comprises a resilient member configured to exert a bias force on the closure lock feature, wherein the firing lockout mechanism is spaced apart from the resilient member.

19. A surgical stapler comprising:
(a) a body, wherein the body includes a body housing and a body frame structure;
(b) a shaft assembly extending distally from the body;
(c) an end effector at a distal end of the shaft assembly, wherein the end effector is actuatable between an open state for receiving tissue and a closed state for clamping the tissue;
(d) a closure system supported by the body frame structure and operatively coupled with the end effector, wherein the closure system is operable to actuate the end effector from the open state to the closed state;
(e) a firing system supported by the body frame structure and operatively coupled with the end effector, wherein the firing is operable to actuate the end of in the closed state to staple the clamped tissue; and
(f) a firing lockout mechanism fully enclosed within the body housing and pivotably coupled to the body frame structure, wherein the firing lockout mechanism is a unitary monolithic structure and is movable relative to the body frame structure between a first position in which the firing lockout mechanism inhibits actuation of the firing system, and a second position in which the firing lockout mechanism permits actuation of the firing system, wherein the firing lockout mechanism is resiliently biased toward the first position,
wherein the firing lockout mechanism is configured to be driven into the second position and thereby permit actuation of the firing system in response to the end effector assuming the closed state.

20. The surgical stapler of claim 19, wherein the closure system comprises a pivotable closure trigger supported by the body frame structure, wherein the firing lockout mechanism is configured to remain stationary in the first position throughout partial actuation of the closure trigger for partially closing the end effector, wherein the firing lockout mechanism is configured to move to the second position in response to full actuation of the closure trigger for placing the end effector in the closed state.

* * * * *